(12) United States Patent
Sahaf

(10) Patent No.: US 12,393,187 B2
(45) Date of Patent: Aug. 19, 2025

(54) SYSTEMS AND METHODS FOR IDENTIFYING SUBCOMPONENT FAILURE IN SEQUENCING INSTRUMENTS

(71) Applicant: ILLUMINA, INC., San Diego, CA (US)

(72) Inventor: Yasmin Sahaf, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 657 days.

(21) Appl. No.: 17/710,665

(22) Filed: Mar. 31, 2022

(65) Prior Publication Data

US 2022/0317674 A1 Oct. 6, 2022

Related U.S. Application Data

(63) Continuation of application No. PCT/US2022/021813, filed on Mar. 24, 2022.
(Continued)

(51) Int. Cl.
*G06N 5/01* (2023.01)
*B01L 3/00* (2006.01)
*G05B 23/02* (2006.01)

(52) U.S. Cl.
CPC .... *G05B 23/0281* (2013.01); *B01L 3/502715* (2013.01); *G05B 23/0229* (2013.01); *G05B 23/0272* (2013.01); *G06N 5/01* (2023.01)

(58) Field of Classification Search
CPC .......... B01L 3/502715; G05B 23/0229; G05B 23/0272; G05B 23/0281; G06F 11/0754;
(Continued)

(56) References Cited

U.S. PATENT DOCUMENTS 6,125,194 A * 9/2000 Yeh .................... G06T 7/0012
382/132
8,241,573 B2 8/2012 Banerjee et al.
(Continued)

OTHER PUBLICATIONS

Dorgo, Gyula, et al., "Decision trees for informative process alarm definition and alarm-based fault classification", Process Safety and Environmental Protection, Institution of Chemical Engineers, Rugby, GB, vol. 149, Oct. 18, 2020, pp. 312-324.
(Continued)

*Primary Examiner* — Tsung Yin Tsai
(74) *Attorney, Agent, or Firm* — Flaster Greenberg P.C.

(57) ABSTRACT

The technology disclosed relates to systems and methods for diagnosing system malfunction and isolating a cause of system malfunction. The method includes applying preprocessors to time series data. The preprocessors detect time series discontinuities, drift, lack of expected correlation, and trends. The method includes feeding, for at least one image channel in one sequencing run, at least part of the output of the preprocessors to a trained tree-based classifier and receiving a classification of the particular sequencing run as abnormal. The abnormal classification can indicate a system malfunction. The method includes feeding at least part of the output of the preprocessors for the abnormal sequencing run to an expert rule system. The expert rule system can isolate a root cause of the system malfunction to a particular subcomponent in need of adjustment or replacement. The method can generate a notification of the particular subcomponent causing the system malfunction.

36 Claims, 21 Drawing Sheets

Related U.S. Application Data

(60) Provisional application No. 63/169,676, filed on Apr. 1, 2021.

(58) Field of Classification Search
CPC ... G06F 11/079; G06F 11/0793; G06V 10/70; G06V 20/52; G06V 2201/06; G06N 20/00; G06N 5/01; G06N 5/04; G06N 7/01; G16B 30/00; G16H 50/20
See application file for complete search history.

(56) References Cited

U.S. PATENT DOCUMENTS

| | | | |
|---|---|---|---|
| 10,438,036 B1* | 10/2019 | Reome | G06K 7/1404 |
| 11,238,129 B2* | 2/2022 | Jalal | H04L 41/065 |
| 11,308,417 B2* | 4/2022 | Vichare | G06F 11/3089 |
| 2002/0054694 A1* | 5/2002 | Vachtsevanos | G06V 10/421 |
| | | | 382/156 |
| 2009/0228408 A1* | 9/2009 | Kaushal | G06N 5/04 |
| | | | 714/26 |
| 2016/0371316 A1* | 12/2016 | Okanohara | G06N 3/044 |
| 2017/0151565 A1 | 6/2017 | Earney et al. | |
| 2017/0198782 A1* | 7/2017 | Rowlen | G01N 15/1436 |
| 2018/0293722 A1* | 10/2018 | Crocco | G06V 10/82 |
| 2019/0213473 A1* | 7/2019 | Dutta | C12Q 1/6869 |
| 2019/0277913 A1* | 9/2019 | Honda | G01R 31/2894 |
| 2020/0379454 A1 | 12/2020 | Trinh et al. | |
| 2021/0042570 A1* | 2/2021 | Iskandar | G06F 18/285 |
| 2021/0081698 A1* | 3/2021 | Lindeman | G06Q 30/0283 |
| 2021/0088541 A1 | 3/2021 | Apker | |
| 2021/0165708 A1* | 6/2021 | Vijayaraghavan | G06N 3/04 |
| 2021/0278819 A1* | 9/2021 | Elliot | G05B 19/4063 |
| 2022/0100817 A1* | 3/2022 | Jalal | G06F 11/0751 |
| 2022/0317674 A1* | 10/2022 | Sahaf | G16B 30/00 |

OTHER PUBLICATIONS

Dorgo et al., Decision Trees for Informative Process Alarm Definition and Alarm-Based Fault Classifcation:, Oct. 18, 2022, pp. 1-13.

* cited by examiner

Focus and Intensity Scores Time Series For Top and Bottom Surfaces of a Flow Cell Illustrating Signal Discontinuity and Lack of Expected Correlation Training Data Examples (1/3) 525

Primary Metrics ① ② ③
Calculated Features ④

| index | surface | read_num | run_start_date | run_id | serial_num | run_state |
|---|---|---|---|---|---|---|
| 0 | 2 | 1 | 6/27/2018 9:38 | 100142044 | M01596 | Completed |
| 1 | 2 | 2 | 6/27/2018 9:38 | 100142044 | M01596 | Completed |
| 2 | 2 | 2 | 1/2/2015 10:42 | 10017008 | M02534 | Completed |

| size | q30 | aligned_percent | error_rate |
|---|---|---|---|
| 1176761013 | 89.98044 | 3.001427 | 1.601657 |
| 1176761013 | 89.98044 | 3.001427 | 1.601657 |
| 3066798818 | 90.00719 | 2.74108 | 2.329751 |

| max_cycle | tile_count | id+read_num+surface |
|---|---|---|
| 80 | 19 | 100142044_1_2 |
| 80 | 19 | 100142044_2_2 |
| 301 | 19 | 10017008_2_2 |

| avg_inten | avg_fs | A_intensity_change | A_fs_change | A_fs_delta_slope |
|---|---|---|---|---|
| 163.9625 | 3.1510366 | 12.02531646 | 0.261841436 | 0.003850604 |
| 160.55 | 3.2234581 | 8.189873418 | 0.181059933 | 0.003794731 |
| 282.1262458 | 3.2388011 | 5.306666667 | 0.051278913 | 0.000225555 |

Connected to Table ⑤

FIG. 5B

Training Data Examples (2/3) 525        Calculated Features ⑤ ⑥ ⑦ ⑧

| A_num_fs_max_bigJump | A_num_fs_min_bigJump | C_intensity_change | C_fs_change |
|---|---|---|---|
| 80 | 80 | 22.44303797 | 0.267848689 |
| 80 | 80 | 16.10126582 | 0.189498529 |
| 301 | 301 | 7.963333333 | 0.050812483 |

| C_fs_delta_slope | C_num_fs_max_bigJump | C_num_fs_min_bigJump | G_intensity_change | G_fs_change |
|---|---|---|---|---|
| 0.0004002382 | 80 | 80 | 15.64556962 | 0.255174617 |
| 0.000430105 | 80 | 80 | 9.569620253 | 0.177410638 |
| 0.000024052 | 301 | 301 | 6.513333333 | 0.064187836 |

| G_fs_delta_slope | G_num_fs_max_bigJump | G_num_fs_min_bigJump | T_intensity_change | T_fs_change |
|---|---|---|---|---|
| 0.0004220486 | 80 | 80 | 20 | 0.275534712 |
| 0.0003879469 | 80 | 80 | 14.86075949 | 0.192271928 |
| 0.000223219 | 301 | 301 | 8.68 | 0.06552342 |

| T_fs_delta_slope | T_num_fs_max_bigJump | T_num_fs_min_bigJump |
|---|---|---|
| 0.0043679 | 80 | 80 |
| 0.0043319027 | 80 | 80 |
| 0.000222478 | 301 | 301 |

Connected to Table ⑨

FIG. 5C

Training Data Examples (3/3) 525        Calculated Features ⑨ ⑩ ⑪ ⑫

| A_correlation | C_correlation | G_correlation | T_correlation |
|---|---|---|---|
| 0.094889396 | 0.109948967 | 0.106410905 | 0.090150071 |
| 0.028884553 | 0.138491764 | -0.066604469 | 0.010490236 |
| 0.189848122 | 0.220114401 | 0.185615525 | 0.215120033 |

⑨

| fs_min_max_surface_diff | Is_M3_Drift |
|---|---|
| 1.3825 | FALSE |
| 1.1925 | FALSE |
| 0.4575 | FALSE |

| A_fs_min | A_fs_max | A_fs_min_max_diff |
|---|---|---|
| 2.67 | 4.14 | 1.47 |
| 2.86 | 4.12 | 1.26 |
| 3.11 | 4.06 | 0.95 |

⑩

| C_fs_min | C_fs_max | C_fs_min_max_diff |
|---|---|---|
| 2.76 | 4.26 | 1.5 |
| 2.97 | 4.24 | 1.27 |
| 3.27 | 4.17 | 0.9 |

| G_fs_min | G_fs_max | G_fs_min_max_diff |
|---|---|---|
| 2.64 | 4 | 1.36 |
| 2.82 | 4.03 | 1.21 |
| 3.1 | 4.03 | 0.93 |

⑪

| T_fs_min | T_fs_max | T_fs_min_max_diff | fs_min_max_diff | label |
|---|---|---|---|---|
| 2.66 | 4.14 | 1.48 | 1.46 | 1 |
| 2.85 | 4.14 | 1.29 | 1.27 | 1 |
| 3.17 | 4.12 | 0.95 | 0.93 | 1 |

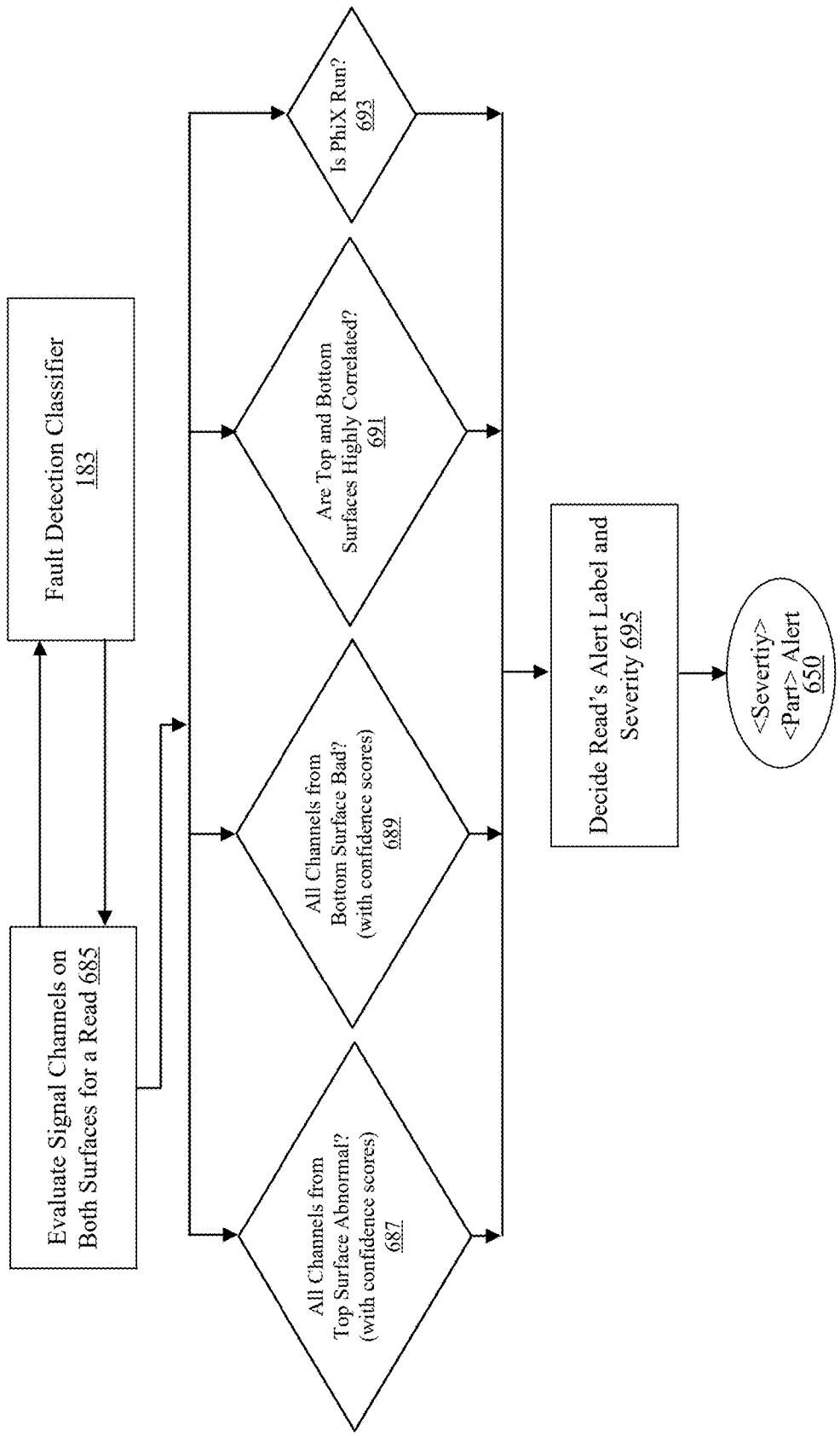

Examples of Alerts Generated

| Component | Severity | Alert summary | Alert Details |
|---|---|---|---|
| M3 | Info ⓘ | Potential Optics problem. M3 is more likely to be the cause, < Additional Alert Details> | - Problem detected in one Camera. |
| M3 | Warning ⚠ | Potential M3 problem. < Additional Alert Details> | - Problem detected in one Camera. Q30 out of spec. or - FWHM drift detected in one camera |
| Z Stage | Info ⓘ | Potential Optics problem. Z-stage is more likely to be the cause, < Additional Alert Details> | - Problem detected in one LED color pair |
| Z Stage | Warning ⚠ | Potential Z-stage problem. < Additional Alert Details> | - Problem detected in one LED color pair. Q30 out of spec. or - Problem detected in FWHM only on top surface |
| Compensator | Info ⓘ | Potential Optics problem. Compensator or Z-stage is more likely to be the cause, < Additional Alert Details> | - Problem detected in FWHM only on bottom surface |
| Compensator | Warning ⚠ | Potential Compensator problem, Z-stage might bet at fault as well. < Additional Alert Details> | - Problem detected in FWHM only on bottom surface. |

Info Next Step : Monitor performance and investigate if no-site. It is more likely to be related to the part flagged.
Critical Next Step : A case is created automatically, check the optics system, the problem is more likely to be related to the part flagged.

FIG. 7A

SYSTEMS AND METHODS FOR IDENTIFYING SUBCOMPONENT FAILURE IN SEQUENCING INSTRUMENTS

PRIORITY APPLICATION

This application is a continuation of, and claims priority to and the benefit of, International Application No.: PCT/US2022/021813, entitled "SYSTEMS AND METHODS FOR IDENTIFYING SUBCOMPONENT FAILURE IN SEQUENCING INSTRUMENTS," filed Mar. 24, 2022, which claims the benefit of U.S. Provisional Patent Application No. 63/169,676, entitled "SYSTEMS AND METHODS FOR IDENTIFYING SUBCOMPONENT FAILURE IN SEQUENCING INSTRUMENTS," filed Apr. 1, 2021. The priority applications are incorporated by reference for all purposes.

FIELD OF THE TECHNOLOGY DISCLOSED

The technology disclosed is related to application of machine learning-based classifiers and expert systems to identify subcomponents causing failure of subsystems in sequencing systems. This technology can be extended to identification of subcomponents causing failure of other types of systems.

BACKGROUND

The subject matter discussed in this section should not be assumed to be prior an merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

The technology disclosed relates to sequencing systems including systems applying sequencing-by-synthesis technique for sequencing nucleotides. A sequencing run to identify nucleotides in molecules is an extended process taking multiple days to complete. All subsystems of a sequencing machine need to operate without errors in order for resulting base calls to be useful for downstream analytics. The subsystems can have multiple subcomponents. The output from sequencing instruments describing quality of sequencing runs does not help in identification of a subcomponent causing system malfunction. A significant percentage of service calls have been observed to result in incorrect subcomponent replacement thus causing significant loss to operators of such instruments.

Accordingly, an opportunity arises to develop systems and methods to identify subcomponent causing malfunction of a sequencing instrument.

BRIEF DESCRIPTION OF THE DRAWINGS

FIGS. 5B, 5C, and 5D present example data values for primary metrics and calculated features for training the fault detection classifier.

FIGS. 6A, 6B, and 6C present processing of classifications of multiple signal channels for one read (FIG. 6C), then combined across two reads in a sequencing run (FIG. 6B) and finally across multiple sequencing runs (FIG. 6A) to isolate a subcomponent causing failure.

FIG. 7A presents examples of alerts generated by the system including the malfunctioning subcomponent, severity, alert summary, and alert details.

DETAILED DESCRIPTION

Figure 1:
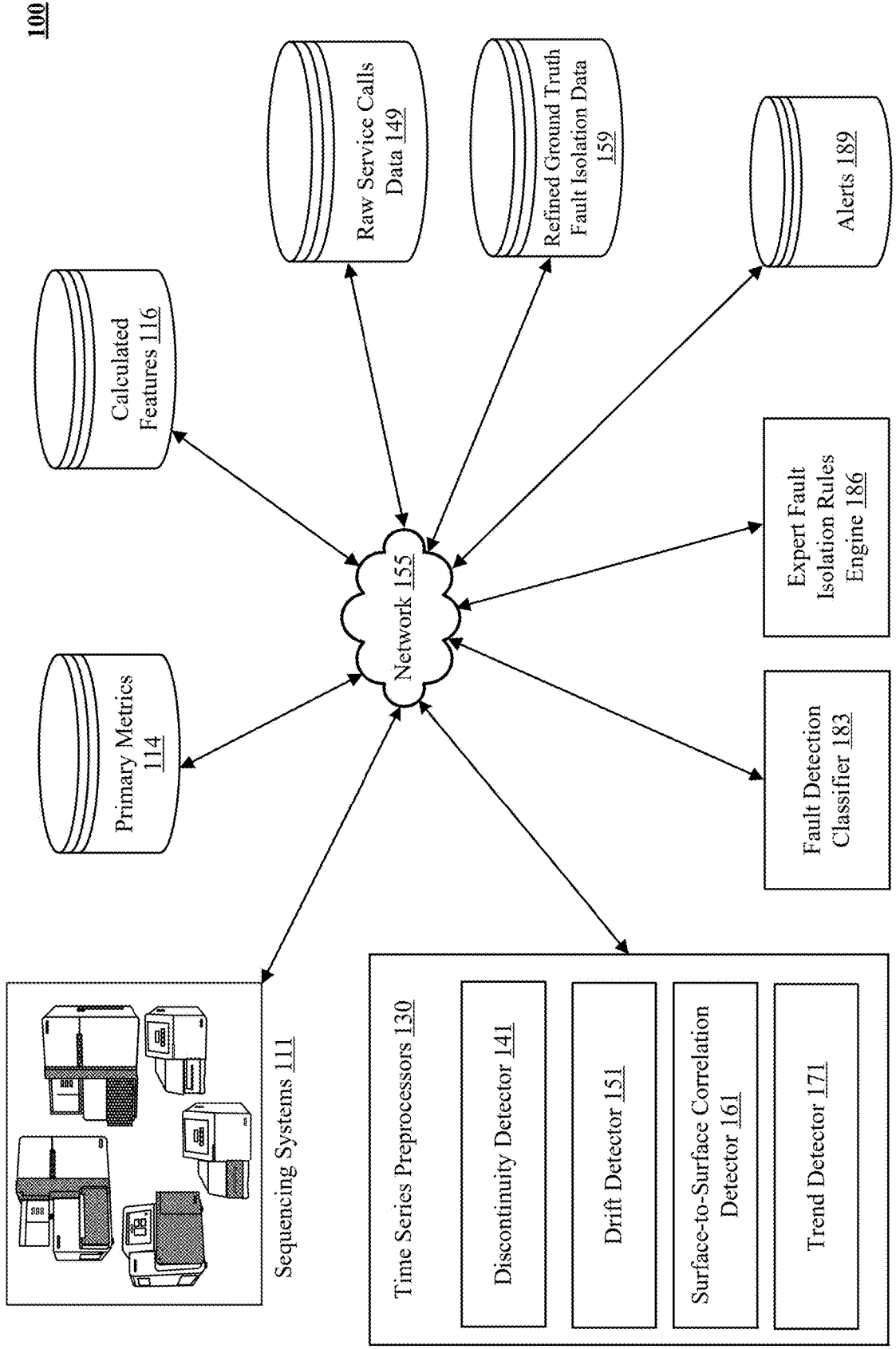
FIG. 1 shows an architectural level schematic of a system that can classify time series data from sequencing instruments and isolate root cause of system malfunction.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

Sequencing-by-synthesis (SBS) is one of several popular techniques for sequencing nucleotides in a DNA or RNA molecule. The machines that perform sequencing are complex systems comprising sophisticated subsystems that have replaceable subcomponents. These sequencing machines can include subsystems containing flow cells, fluidics and reagents, optics and image capture, and processing modules. These sequencing systems apply SBS techniques for base calling cycles in a sequencing run. In SBS process cycles, complementary nucleotides are added, one at a time, to a nucleotide sequence fragment (also called as a molecule or an insert) from the sequence being processed. Sequencing nucleotides in molecules proceeds in hundreds of cycles. A cycle includes chemical, image capture and image processing actions. The subsystems and their subcomponents operate in each cycle to identify a tagged complementary nucleotide attached to molecules.

The optics subsystem includes, for instance, M3, z-stage, and compensator subcomponents used to image the flow cells. The images record glow from clusters of A, C, G, and T bases that have fluorescently tagged complimentary nucleotides, with fluorophores temporarily attached for the synthesis cycle. The M3 subcomponent includes a mirror used for focus of a mono-chromatic excitation beam or light from a laser or an LED source to excite the fluorescent tags. The z-stage subcomponent moves an objective lens up and down along a z-axis for gross focus of a camera capturing images. Clusters of molecules can grow on both top and bottom surfaces of the flow cells. The compensator subcomponent provides fine focus between top and bottom surfaces of the flow cells, which are separated by about one-tenth of a millimeter. It handles changing focus from one surface to the other of the flow cell.

Failure of any of these subcomponents can cause poor focus quality and degradation of image intensity. Information collected to perform sequencing is not designed to isolate failure of subcomponents. The relationship of some of sequencing quality-related information to subcomponent failure and fault isolation is obscure. Technicians who use overall sequencing confidence scores to confirm that a machine is malfunctioning often pick the wrong subcomponent to replace and end up replacing multiple subcomponents when only one was at fault. A significant percentage of service calls have been observed to result in incorrect subcomponent replacement thus causing significant loss to operators of such instruments. It is therefore desired to develop systems and techniques to reliably identify the subcomponent causing a malfunction of the optics subsystem.

With carefully refined ground truth fault isolation data, refined to be better than typical technician performance in the field, expert systems can be trained to recognize signal patterns that characterize failures in particular subcomponents. In stages, the technology disclosed incudes a fault detection classifier and expert fault isolation rules. Classifier architectures (such as random forest) are selected that can be trained with small data sets to recognize a serviceable fault, which is further processed against hand crafted expert rule sets. The expert rules suggest which subcomponent to replace and present reasoning embodied in the rule that is applied. With a larger training data set, the two stages could be combined into a single classifier. Technicians guided by expert system fault isolation are more likely to replace the right subcomponent.

Raw ground truth data, indicating what subcomponents technicians historically decided to replace, is not reliable, due to the fault isolation error rate. Moreover, compared to the number of sequencing runs available, the sample size of equipment repairs is small, because sequencing equipment is reliable. Cleaning the raw ground truth data, by correctly labeling collected time series data with subcomponent failures, is more productive than discarding suspicious data. Additional description of the time series data puts this in perspective.

In a sequencing run, multiple signal channels generate time series data. This is true of SBS and other sequencing techniques. Sequencing segments of a molecule with 350 nucleotides by SBS can involve 300 or more processing cycles in a sequencing run. A sequencing run can be divided into two reads (read 1 and read 2) proceeding from the 3' and the 5' ends of the same sequence fragment and either overlapping or leaving a gap in the middle of the fragment. Throughout a read, each cycle includes imaging top and bottom surfaces of the flow cell and collecting data. The sequencing instrument can provide data such as full-width-at-half-max (or FWHM) values indicating the focus quality and image intensity values per sequencing cycle. Some sequencing instruments use nucleotides labeled with four different colored fluorescent dyes corresponding to A, C, G, T nucleotides. In such sequencing instruments, four signal (or image) channels can be used to identify four types of nucleotides. Therefore, there can be up to eight time series per flow cell surface in a sequencing read (1 read×2 signal types×4 signal channels). For a flow cell with two surfaces there can be up to sixteen time series. Such instruments can use one or two laser or LED light sources to excite the fluorescent tags corresponding to A, C, G, T nucleotides. The time series data for each signal channel in a successful sequencing run follows a characteristic signal pattern. Deviation of a given signal channel from respective signal pattern can indicate a potential problem.

Some sequencing instruments can use fewer than 4 signal channels to identify four types of nucleotides. For example, some sequencing instruments can use two signal channels to detect four types of nucleotides (A, C, G, T). In such systems, two images are taken per cycle. A first nucleotide type is detected in a first channel, a second nucleotide type is detected in a second channel, a third nucleotide type is detected in both the first, and the second channel and a fourth nucleotide type that lacks a dye-tagged label, is not, or minimally, detected in either channel. The technology disclosed can process time series for signal channels for the four types of nucleotides to detect subcomponent malfunction.

In yet another type of sequencing instruments, one signal channel can be used to detect four types of nucleotides. Such sequencing systems can include patterned flow cell with nanowells fabricated over CMOS chip. The sequencing instrument can use one fluorescent dye, two chemistry steps and two imaging steps per cycle. In one example, the four types of nucleotides are detected as following. A first nucleotide (e.g., "A" base) has a removable label and is labeled in the first image only. A second nucleotide (e.g., "C" base) can have a linker group that can bind a label and is labeled in the second image only. A third nucleotide (e.g., "T" base) can have a permanent fluorescent label and is therefore labeled in both images. A fourth nucleotide (e.g., "G" base) is permanently dark. The four nucleotides are detected by analysis of different emission patterns for each base across the two images. The technology disclosed can process time series for signal channels for the four types of nucleotides to detect subcomponent malfunction.

Time series data from at least one signal channel are preprocessed to prepare training data for the classifier. It is challenging to identify features in time series data related to specific subcomponent failure. The technology disclosed was developed using graphical representations of time series data to identify features that can isolate a subcomponent causing failure. Applying feature engineering during signal preprocessing, patterns observed from subcomponents that were faulty produced discontinuities, out of range signals, bad correlations between two surfaces, and signal trends. Abnormal sequencing runs are indicated or at least suggested when these patterns in time series data are detected. Respective patterns indicate abnormality caused by various subcomponents. Some of the training examples are relabeled, correcting, when appropriate, labeling of the subcomponent that needed to be replaced. The signal patterns are plotted and visually inspected for signal characteristics. Programmatic detectors are developed to calculate the features used to isolate subcomponents causing malfunction. Examples of programmatic signal pattern detectors include a discontinuity detector, a drift detector, a surface-to-surface correlation detector, and a trend detector. Programmatic detectors are applied to time series data from multiple signal channels to generate calculated features used by the fault detection classifier and then by expert fault isolation rules. The details of signal detectors are presented below.

The discontinuity detector identifies big jumps between successive cycles, for instance, in focus scores. Big jumps can indicate large variations in time series data between successive cycles. For example, difference between focus score values of successive cycles can indicate a big jump when the calculated difference is above a predetermined threshold. The surface of the flow cell may not be optically flat across imaging tiles. During imaging step, z-stage subcomponent can adjust the height of the objective lens from tile to tile to accommodate uneven surface of flow cell. A faulty z-stage subcomponent can result in incorrect focus of image tiles resulting in discontinuities (or jumps) in the focus scores time series for multiple image channels.

In each cycle, the z-stage is used to move the objective lens and adjust the optical focus when the LED color changes between green and red. A malfunction in the z-stage between LED activations degrades focus, which is reflected in an abrupt increase in the focus score, in the FWHM statistic for the tile being imaged. Because the beam from each LED activation is split along two paths and detected by at least one camera, the impact of z-stage malfunctioning can be observed in FWHM values from images taken by both cameras. An expert rule isolates the z-stage as a likely cause of malfunctioning when such discontinuities are detected.

The drift detector compares drift over time in signals captured by cameras on different optical paths, in order to isolate malfunctioning of a component present in one optical path but not the other. The M3 mirror, in some systems, is present on one optical leg. It has an overall focus role and a single leg focus role. When the single leg focus is malfunctioning, images from both red and green actuations of one camera suffer a focus score or FWHM statistic degradation, relative to the other camera. An expert rule isolates the M3 mirror as a likely cause of malfunctioning when differential drift between signals from respective cameras is detected.

The surface-to-surface correlation detector detects whether signal channels for a top surface of the flow cell follow a similar signal pattern to corresponding signal channels for a bottom surface of the flow cell. When the optical subsystem components are working normally, the corresponding signal channels for top and bottom surfaces follow a similar signal pattern. Failure of optical system subcomponents can cause variation in signal channel pattern between the top and bottom surfaces. Expert rules can check whether multiple signal channels from one surface (such as the top surface) are classified as abnormal, and whether two surfaces of the flow cell have a low correlation. If these conditions are true, the expert isolation rules can isolate the compensator subcomponent as a likely cause of system malfunction.

The trend detector can identify degrading focus when the focus score values in a last part of the focus scores time series are degraded relative to focus score values in a first part of the focus scores time series. The trends for time series corresponding to multiple signal channels can be given as input to fault detection classifier along with other inputs for classifying the signal channels as normal or abnormal. The trend calculated feature can be used as input to one or more expert rules. However, it is primarily used by the first stage random forest classifier to classify a signal channel as normal or abnormal.

The technology disclosed can also include a mid-process vibration detector to detect a feature in focus scores time series from at least one signal channel indicating a z-stage subcomponent failure. The focus scores time series in such z-stage malfunction can include a middle part with discontinuities or spikes. The middle part is positioned in between a first and second good parts of focus scores time series. The two good parts can include focus score values that are mostly within the normal focus scores range. The detector can return a "true" result when it detects a mid-process vibration with higher average focus scores (or FWHM) in a focus scores time series. Expert fault isolation rules engine can use the output from the mid-process vibration detector to generate an alert for z-stage subcomponent malfunction.
Environment We describe a system for diagnosing system malfunction and isolating a cause of system malfunction among a plurality of replaceable subcomponents. Sequencing-by-synthesis (SBS) is a technique of sequencing nucleotides in a DNA or RNA molecule. SBS involves adding complementary nucleotides, one at a time, to a nucleotide sequence fragment from the DNA or RNA molecule to be sequenced. An optical platform using SBS can sequence billions of clusters of nucleotide sequence fragments, sometimes called molecules, on a surface of a flow cell, arranged in multiple lanes with tiles in each lane. Molecule clusters present clones of a molecule. Cloning a molecule amplifies signals generated during SBS. The system is described with reference to FIG. 1 showing an architectural level schematic of a system in accordance with an implementation. Because FIG. 1 is an architectural diagram, certain details are intentionally omitted to improve the clarity of the description. The discussion of FIG. 1 is organized as follows. First, the elements of the figure are described, followed by their interconnection. Then, the use of the elements in the system is described in greater detail.

FIG. 1 includes the system 100. This paragraph names labeled parts of system 100. The figure illustrates sequencing systems 111, a primary metrics database 114 for storing metrics collected from sequencing instruments, a calculated features database 116, time series preprocessors 130, a raw service calls database 149, a refined ground truth fault isolation database 159, a fault detection classifier 183, an expert fault isolation rules engine 186, an alerts database 189 and a network(s) 155. The time series preprocessors 130 further include programmatic detectors to calculate features from time series data from reads in sequencing runs. The system includes a discontinuity detector 141, a drift detector 151, a surface-to-surface correlation detector 161 and a trend detector 171. The calculated features generated by time series preprocessors are used by fault detection classifier and then by expert fault isolation rules engine to isolate a subcomponent causing malfunction of a sequencing instrument.

The technology disclosed applies to a variety of sequencing systems 111, also referred to as sequencing instruments or sequencing platforms. Some examples of sequencing systems 111 include Illumina's MiSeqDx™, NovaSeq 6000™, HiSeqX™, HiSeq3000™, and HiSeq4000™. These sequencing systems are configured to apply sequencing-by-synthesis (SBS) technique for base calling. The network(s) 155 couples the sequencing systems 111, the primary metrics database 114, the calculated features database 116, time series preprocessors 130, the raw service calls database 149, the refined ground truth fault isolation database 159, the fault detection classifier 183, the expert fault isolation rules engine 186, and the alerts database 189, in communication with one another.

Before the sequencing cycles begin, a library of molecules to be sequenced is prepared on a slide or a flow cell. The molecules are arranged in tiles within multiple lanes on one or two surfaces of a flow cell. A cycle includes chemical, image capture and image processing actions. Subsystems, including optical, mechanical, and chemical subsystems, operate in each cycle to identify the complementary nucleotide attached to molecules. A sequencing run can include hundreds of cycles, sometimes performed in two reads proceeding from 3' and 5' ends of the same sequence fragment. Sequencing runs can take multiple days to complete. Sometimes, results of an entire sequencing run are discarded because they do not meet the minimum quality requirements for downstream analysis.

The sequencing instruments produce several outputs (also referred to as primary metrics) after scanning and imaging of the flow cell surfaces is completed. Examples of outputs from the instrument include full-width-at-half-max (of FWHM) values indicating the focus quality and image intensity values per sequencing cycle. Other examples of primary metrics include a read number (such as 1 or 2), a surface identifier (such as 1 or 2), a sequencing run identifier, serial number of the instrument, a run state indicating whether the run "completed" or "stopped" before completion. The primary metrics can also include the quality score (such as Q30 score) for the sequencing run, a percentage of sequence aligned, an error rate, a maximum number of cycles in the sequencing run, a count of tiles on the flow cell surface, etc. Primary metrics provide useful information regarding a sequencing run but are not intended to identify a subcomponent in a subsystem causing malfunction or failure.

In SBS, LED light sources or lasers are used to illuminate dye-tagged complementary nucleotide attached to molecules during each cycle. A camera takes images of tiles containing clusters of molecules. The images are then processed to identify a nucleotide (A, C, G, T) attached to the molecules in a cluster. Some sequencing systems use four-channels to identify four types of nucleotides (A, C, G, T) attached to molecules per cycle. In such systems, four images are produced, each image comprises signals having a single distinct color per image. The four colors correspond to the four possible nucleotides present at a particular location. In another type of sequencing systems two channels are used to identify four types of nucleotides (A, C, G, T). In such systems, two images are taken per cycle. A first nucleotide type is detected in a first channel, a second nucleotide type is detected in a second channel, a third nucleotide type is detected in both the first, and the second channel and a fourth nucleotide type that lacks a dye-tagged label, is not, or minimally, detected in either channel.

The optics subsystem includes subcomponents to image the tiles on surface of flow cells. Failure in any of these subcomponents can cause poor focus quality and degradation of image intensity. The sequencing data provided by the instruments is not helpful in isolating a subcomponent causing system malfunction. Therefore, technicians often pick a wrong subcomponent to replace and end up replacing multiple subcomponents when only one was at fault. The raw service calls data stored in the raw service calls database 149 is therefore not reliable for use as ground truth. The system cleans the raw ground truth data by correctly labeling the subcomponent causing malfunction. The system stores the correctly labeled the service calls data in the refined ground truth fault isolation database 159. For the correctly labeled ground truth data, the system applies time series preprocessors 130 to generate calculated features and stores them in a calculated features database with labels indicating successful or failed sequencing run. The technology disclosed can include four types of time series preprocessors producing respective calculated features.

The system applies a trained fault detection classifier 183 and the expert fault isolation rules engine 186 in a two-stage process to isolate subcomponents causing system malfunction. The classifier (such as a random forest) can be trained using a small training set with cleaned ground truth labels indicating a serviceable fault caused by a subcomponent. The trained fault detection classifier 183 can classify a signal channel as normal or abnormal. The classifications of signal channels and calculated features are further processed against hand crafted expert rules by the expert fault isolation rules engine 186 to suggest which subcomponent to replace and present reasoning embodied in the rule that is applied. The system can generate alerts indicating the subcomponent name and severity level of the alert such as warning or information. A service ticket can be opened for the subcomponent maintenance depending on the severity level of the alert.

Completing the description of FIG. 1, the components of the system 100, described above, are all coupled in communication with the network(s) 155. The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN)), Session Initiation Protocol (SIP), wireless network, point-to-point network, star network, token ring network, hub network, Internet, inclusive of the mobile Internet, via protocols such as EDGE, 3G, 4G LTE, Wi-Fi and WiMAX. The engines or system components of FIG. 1 are implemented by software running on varying types of computing devices. Example devices are a workstation, a server, a computing cluster, a blade server, and a server farm. Additionally, a variety of authorization and authentication techniques, such as username/password, Open Authorization (OAuth), Kerberos, Secured, digital certificates and more, can be used to secure the communications.

We present an overview of the subcomponents in the optical subsystem of a sequencing instrument. This is followed by description of details of the time series preprocessors to generate calculated features from the time series data. We then present the two-stage architecture to classify the time series data for multiple signal channels and using the classifications to isolate a subcomponent causing system malfunction.

Optical Subsystem Subcomponents

Figure 2A:
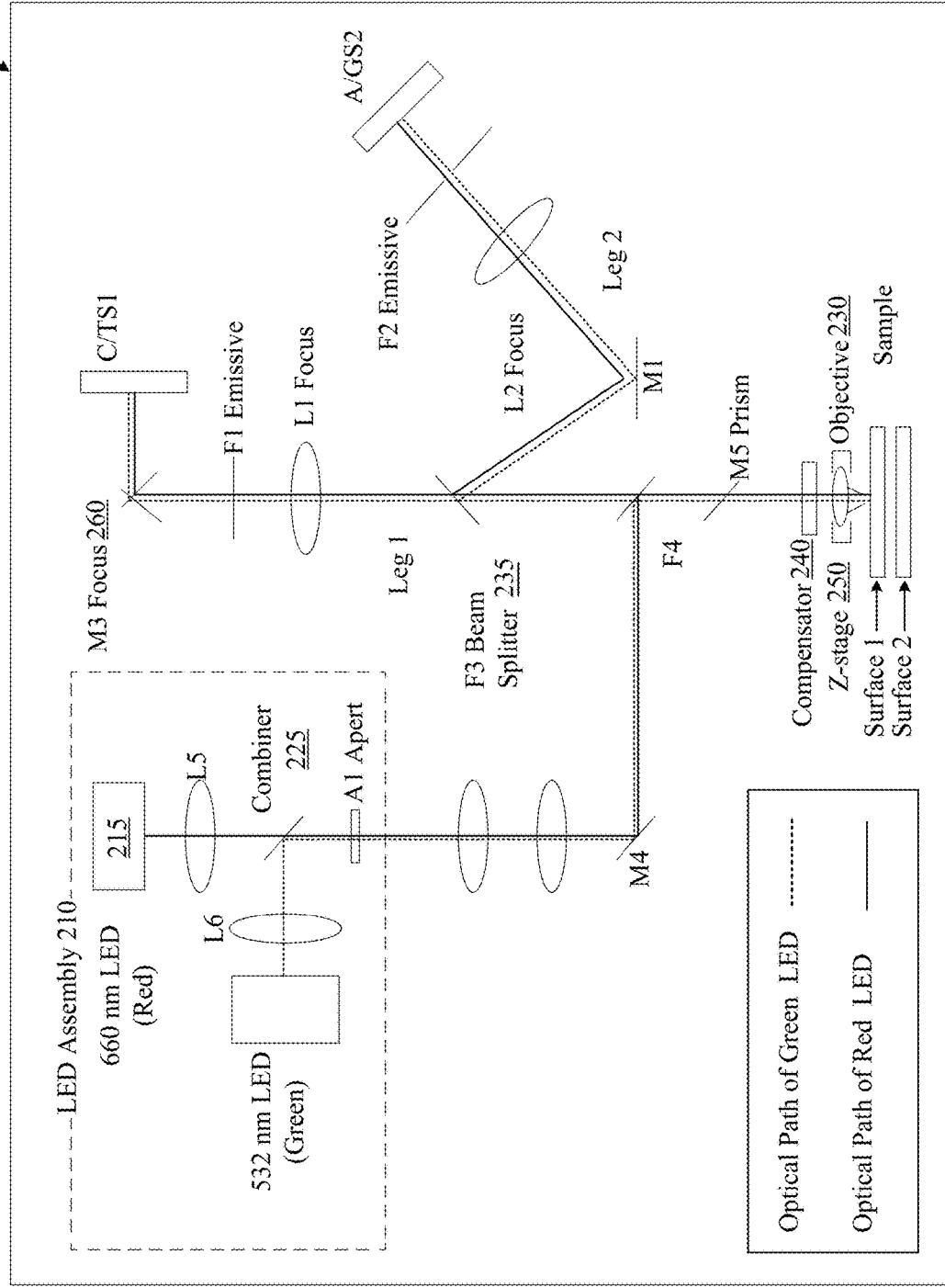
FIG. 2A presents a schematic of subcomponents of an optical subsystem in a sequencing instrument.

FIG. 2A presents illustration of an optical subsystem 205 of a sequencing instrument. We first describe the optical path from radiation source to the imager and then present details of three subcomponents of the optical subsystem. The optical subsystem comprises an LED assembly 210 with radiation source including two light emitting diodes (LEDs) 215 and 220 which produce radiation at different wavelengths from each other. For example, a green LED with a wavelength of 532 nano meter (nm) and a red LED with a wavelength of 660 nm can be used. The optical path of green LED is illustrated using a broken line and the optical path of red LED is illustrated using a solid line. Excitation light from LEDs passes through a green LED collector lens (L6) and a red LED collector lens (L5), respectively. An LED fold mirror reflects the green excitation radiation to a combiner dichroic 225. The green excitation radiation passes through M5 prism which reflects the green excitation through an objective lens 230. The red excitation radiation passes from the LED collector lens L5 to the combiner 225 after which the red excitation radiation follows the same path as the green excitation radiation.

The objective lens 230 is positioned to collect emission radiation and direct it to excitation/emission dichroic (M5 prism) which passes the emission radiation through F3 beam splitter 235 to image sensors S1 and S2. The sample can be positioned on one or more surfaces of the flow cell. The surfaces of flow cell are not optically flat. A z-stage subcomponent 250 is coupled to at least a part of the objective lens and configured to translate the objective lens 230 up and down (along the z-axis) to adjust the position of the objective lens as images of tiles on surfaces of flow cell are captured. An aperture (labeled "A1 Apert") can couple the green and red LED outputs to form a single beam of illumination.

The sample can be positioned at two opposing inner surfaces (surface 1 and surface 2) of a flow cell as shown in FIG. 2A. A compensator 240 can be included in or removed from the optical path to shift the focus of the objective lens from one surface to the other. For example, a compensator (such as a lens) positioned in the optical path can shift the focus of objective to surface 2 and when removed from the optical path, the focus of the objective shifts to surface 1. A mechanical assembly can be coupled to the compensator.

The example optical subsystem in 205 uses two LEDs of different wavelengths to illuminate the fluorescently tagged nucleotides. Two cameras S1 and S2 each capture an image after illumination of the sample using one LED. For example, when red colored excitation laser illuminates the sample, the images from cameras S1 and S2 are used to detect C and A bases, respectively. When green colored excitation laser illuminates the sample, images from cameras S1 and S2 can be used to detect T and G bases, respectively. The F3 beam splitter divides the emission radiation to two optical legs labeled as leg 1 and leg 2. The emission radiation in each leg passes through focus lenses L1 and L2 respectively, followed by F1 emissive and F2 emissive filters.

In a four-dye system, four distinct colors can be used for calling the DNA bases. In such a system, each of the four nucleotides can be labeled with a separate dye. In one cycle, the radiation signals from these dyes are imaged by using two excitation lasers, a red 660 nm frequency laser and a green 532 nm frequency laser. When the sample is illuminated by the red excitation laser, the emission radiation is split in two legs with half of the emission light towards each camera. The emissive filters F1 and F2 are selected to detect emission wavelength corresponding to C and A basis by cameras S1 and S2 respectively. A separate set of emissive filters F1 and F2 can be selected for detecting T and G bases when green excitation laser illuminates the sample. Each image corresponds to a specific combination of an excitation laser and a filter. In one example, emissive filters comprise Bandpass filters of 557±11 nm (to detect signal channel G), 615±40 nm (to detect signal channel T), 684±11 nm (to detect signal channel A), and 740±50 nm (to detect signal channel C). The technology disclosed can process signal channels from other systems including one dye, two dye or three dye systems.

Figure 2B:
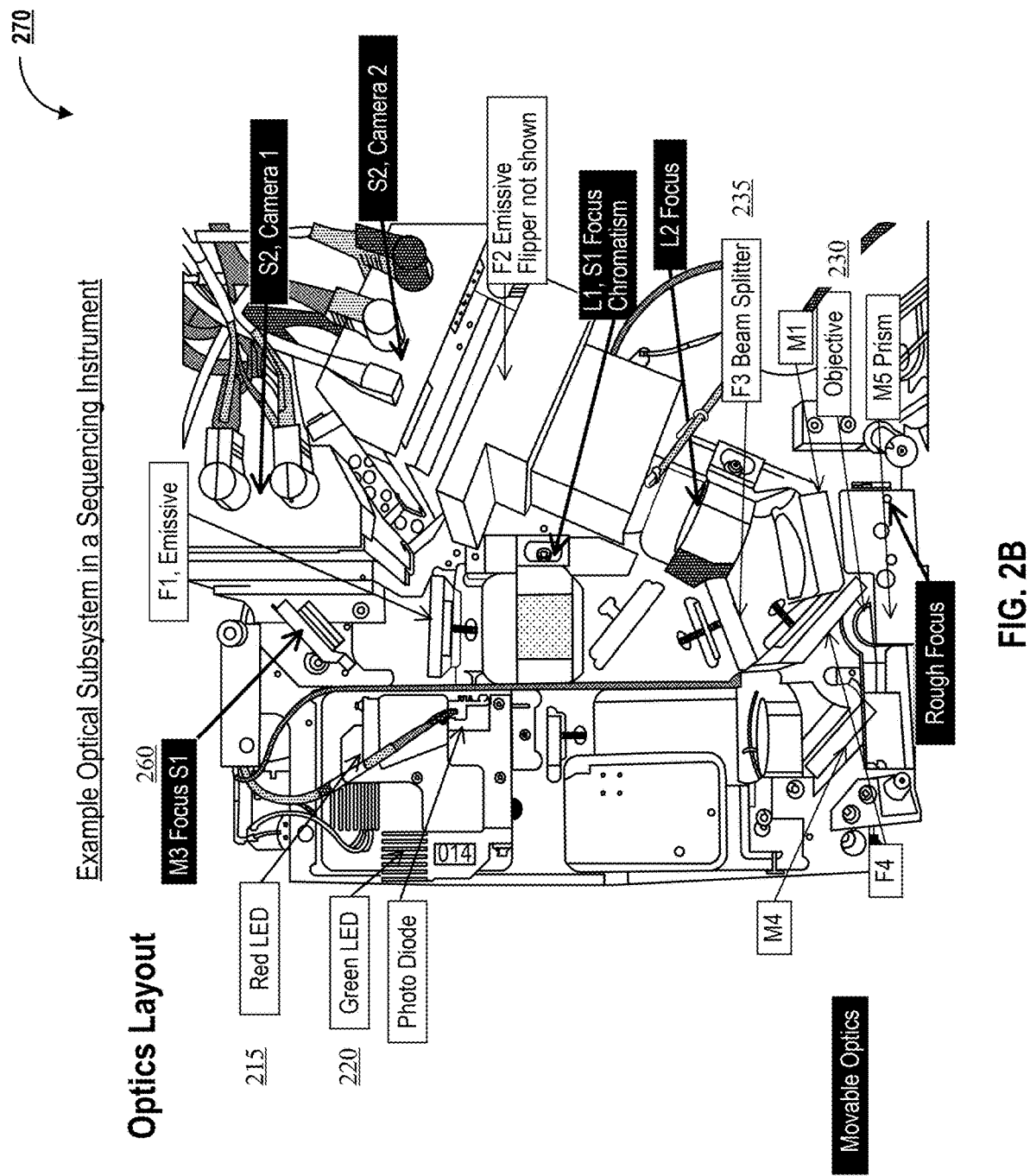
FIG. 2B presents a photographic image of an optical subsystem in a sequencing instrument.

FIG. 2B presents a photographic image 270 of an example optical subsystem in a sequencing instrument. Positions of at least some of the subcomponents from the schematic in FIG. 2A are labeled on the photographic image in FIG. 2B.

M3 Mirror Subcomponent

Referring to the schematic in FIG. 2A, one of the two optical legs can have an M3 focus mirror 260 positioned in the optical path. For example, in optical subsystem 205, the M3 focus mirror is positioned in leg 1. The M3 mirror has an overall focus role and a single leg focus role. The M3 mirror is actuated and can be rotated between two mechanical positions. In an imaging mode, the M3 mirror is positioned at its "imaging position" and acts as 45-degree fold mirror in optical path for camera S1. In a focus mode, the M3 mirror is positioned at its "focus position" and induces a horizontal focus gradient across the image. During focus mode, lasers of different wavelengths (red, green and blue) are reflected from M3 mirror and z-stage is moved up and down to obtain the best focus image. When the single leg focus is malfunctioning, images from both red and green actuations of one camera suffer a focus score or FWHM statistic degradation, relative to the other camera. An expert rule can isolate the M3 mirror as a likely cause of malfunctioning when differential drift between signals from respective cameras is detected.

Z-Stage Subcomponent

Figure 3A:
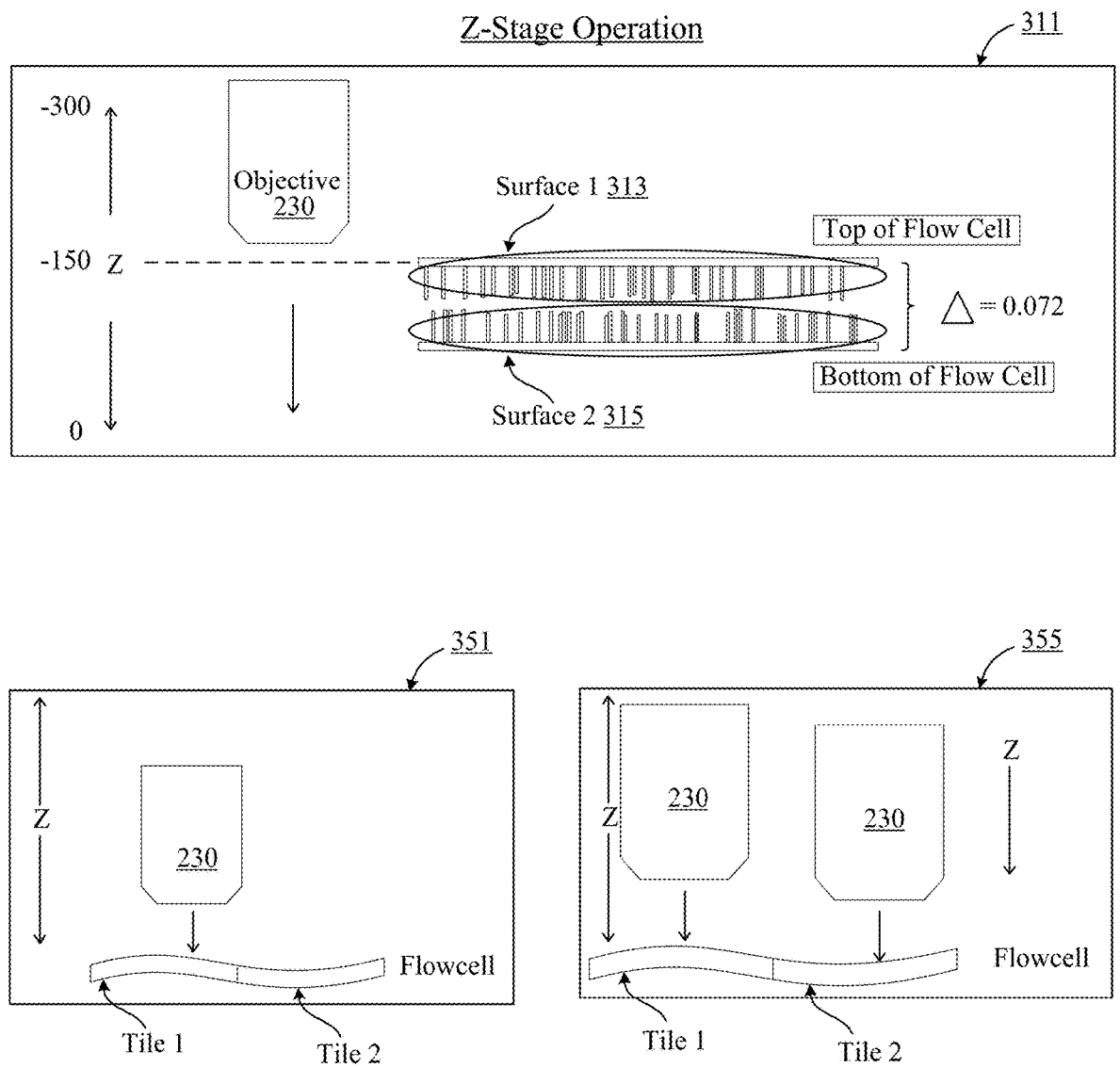
FIG. 3A presents operation of a z-stage subcomponent to move the objective lens to adjust focus from tile to tile on a surface of a flow cell.

FIG. 3A illustrates operation of a z-stage subcomponent 250. A schematic 311 shows the movement of the objective lens along z-axis. Sample is positioned on the two inner surfaces of the flow cell, i.e., surface 1 313 and surface 2 315. Surface 1 is positioned towards the top end of the flow cell and the surface 2 is positioned towards the bottom end of the flow cell. The distance between the two surfaces is small, e.g., about 0.72 millimeters (mm). The z-stage (not shown) can be coupled to the objective lens to move the objective lens along z-axis which is normal to the surface of flow cell. The movement of z-stage can be created by energizing piezo crystals within a mechanical enclosure. The movement of z-stage along z-axis is about 300 micrometers. The upper most position is −300 micrometer from the lowest position (labeled with 0). Clusters of the sample on the inner side of bottom surface of the flow cell are positioned at 0.072 mm below the top surface.

The surface of the flow cell may not be optically flat. During the imaging step the objective lens is positioned above each tile in the flow cell to take the image of the sample. The illustration 351 shows two tiles (tile 1 and tile 2) such that tile 1 is closer to object 230 as compared to tile 2. The z-stage subcomponent maintains focus from tile to tile by moving the objective lens 230 farther or closer to the surface of the flow cell to accommodate bumps in the surface as shown in illustration 355. A faulty z-stage subcomponent can result in degradation of focus scores of images of tiles.

Compensator Subcomponent

Figure 3B:
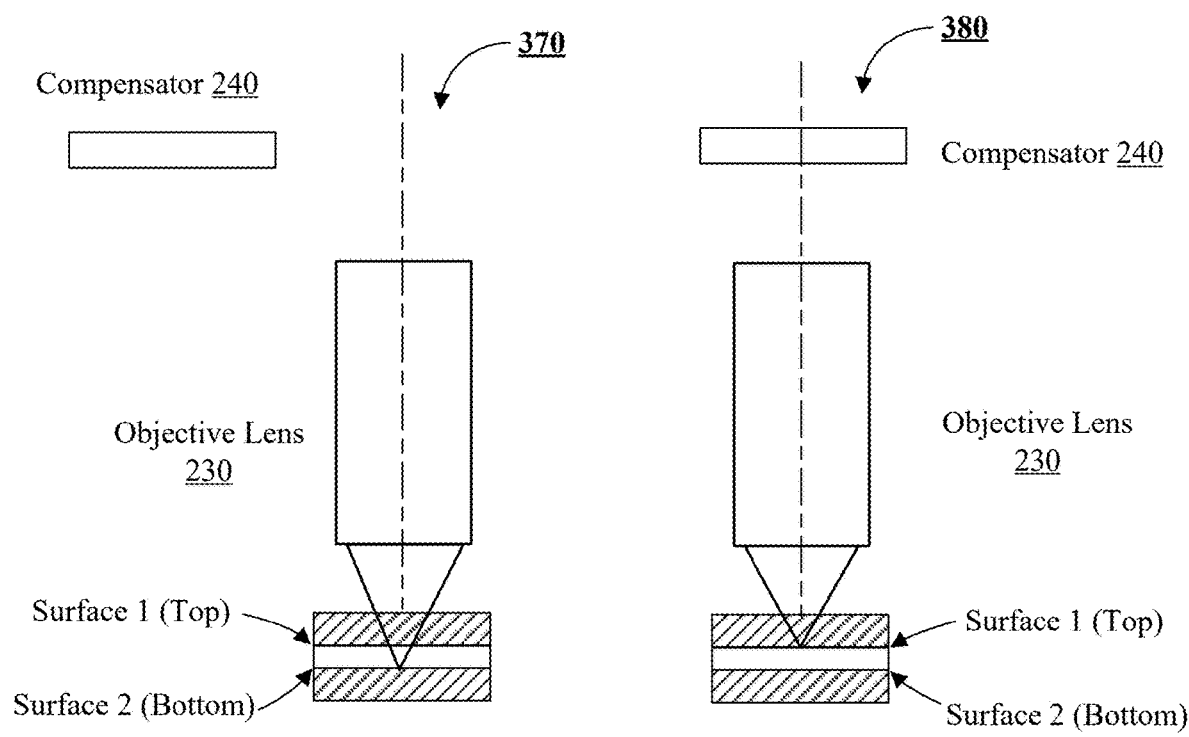
FIG. 3B presents operation of a compensator subcomponent to shift the focus from one surface of the flow cell to another surface.

FIG. 3B illustrates operation of a compensator subcomponent 240. Without a compensator positioned in the optical path, the objective lens 230 may focus and detect images from the bottom surface (or surface 2) of the flow cell as shown in illustration 370. Positioning a compensator 240 in the optical path shifts the focus of objective lens 230 to the top surface (or surface 1) of the flow cell as shown in illustration 380. The objective lens can then detect images from the top surface. The compensator subcomponent can include a mechanism to move the compensator in and out of the optical path as shown in FIG. 3B. Incorrect positioning of compensator can cause degradation of focus scores.

The compensator function can be implemented by using several design alternatives. For example, a correction collar may be positioned in the optical path and adjusted between binary states. For example, a first state may correspond to a situation in which the objective is focused on and detecting images from the bottom surface of flow cell. In a second state of the collar, the objective lens may be focused on and detecting images from a top surface of the flow cell. A malfunctioning compensator can cause incorrect focus shift between the two surfaces. Poor focus scores for images from one surface and lack of expected correlation between focus scores of corresponding signal channels from two surface can indicate compensator subcomponent malfunction.

Examples of Incorrectly Labeled Service Records

A significant percentage of service calls have been observed to result in incorrect subcomponent replacement thus causing significant loss to operators of such instruments. Technicians who use overall sequencing confidence scores to confirm that a machine is malfunctioning often pick the wrong subcomponent to replace and end up replacing multiple subcomponents when only one was at fault.

The service technicians can sometime indicate one or more subcomponents in the "parts replaced" section of the service ticket (or service record) that are not actually replaced or serviced. In some cases, the service technicians select multiple, or all subcomponents related to a subsystem such as optics subsystem in the parts replaced section. When the technicians service the instrument, only one or a few of the subcomponents may be replaced. The "work performed" section of the service records can, in some service tickets, identify subcomponents that were replaced or serviced. The technology disclosed can apply text mining techniques to parse the "work performed" section of service tickets. The "work performed" section includes free form text as shown in service ticket examples below. The new labels extracted using text mining are then used to update labels of training data examples. The correctly labeled training data can be used to generate rules for the expert fault isolation rules engine.

In the following four service calls (Ticket 1 to Ticket 4) M3 subcomponent was selected by service technicians in parts replaced section but after analyzing the description of work performed our technique identified that M3 subcomponent was not the cause of the system malfunction but z-stage subcomponent was likely serviced or replaced by the service technician. We present below the text from work performed section of service records.

Ticket 1: "z stage controller replaced per miseq field service guide pn: 15032181"

Ticket 2: "per field service guide, replaced chiller checked chiller temperature, performed full optic tests."

Ticket 3: "replaced main valve, manifold, green line syringe. 7/6 unit still problem pr2 line. line passed vcl. 7/7 replaced pr2 line. ran fluidics test. passed."

Ticket 4: "engineer need replace/fix compensator. instrument contract ended, customer going renew it. rr 270916—checked image failed run doesn't look like compensator issue nearly focus fuzzy edges. tested anyway seems working correctly. optic checked z height top surface −0.13. adjusted along optics. boltpac ran passing. fluidics temp also tested working. z height updated calibration file."

In the following three service calls (Ticket 5 to Ticket 7) z-stage subcomponent was selected by service technicians in parts replaced section but after analyzing the description of work performed our technique identified that z-stage subcomponent was not the cause of the system malfunction.

Ticket 5: "replaced y-stage, m3 mirror motor, mirror, valve manifold."

Ticket 6: "1. replaced m3 motor m3 motor sensor. 2. optical path alignment completed. 3. washing fluidics part vel test.→boltpac/vcl test passed."

Ticket 7: "* found manifold cracked replaced it, aligned optics."

The relationship of some of sequencing quality-related information to subcomponent failure and fault isolation is obscure. Technicians who use overall sequencing confidence scores to confirm that a machine is malfunctioning often pick the wrong subcomponent to replace and end up replacing multiple subcomponents when only one was at fault. Therefore, the technology disclosed cleans the raw ground truth data, by correctly labeling collected time series data with subcomponent failures. We now present the time series preprocessors that can be used to extract features from correctly labeled time series data. We present an example text mining technique that was used to assign subcomponent labels to service tickets.

Text Mining Techniques

We applied text mining techniques to label work performed section of service tickets with the subcomponent at fault. Input to a text mining technique is free form text from "work performed" section of service tickets. Text strings from "work performed" sections are preprocessed before text mining algorithm is applied. Steps 1 through 4 listed below are the preprocessing steps. Step 5 includes text mining and step 6 produces the output.

Step 1 includes normalizing the text to lower case alphabets.

Step 2 includes removing stop words from the string e.g., "the", "and", etc. These are extra words and do not provide useful information for the analysis.

Step 3 includes removing frequent words that are not interesting for our analysis. The interesting words for this analysis can include "m3", "mirror", "optics", "replaced", etc.

Step 4 includes lemmatization or stemming a word. For example, for verbs, the root of the verb is used instead of past tense or future tense of verbs.

After preprocessing, text mining is performed on the text strings. The technology disclosed can apply a variety of available text mining techniques. For example, in one approach, rule-based technique can be used to identify subcomponents and the work performed such as "replaced". In another approach, topic modeling can be applied. However, topic modeling and testing requires larger labeled data for training. In our case we did not have enough labeled data to test all cases with the topic modeling. As more labeled data becomes available this technique can be applied. Other techniques that can be applied include text classification and name entity recognition (NER). NER considers context around entities when parsing the text. We present an example rule-based algorithm to identify M3 subcomponent in the text.

> Step 5 includes using the text mining algorithm below for identifying a subcomponent. Similar rule-based algorithms can be used to identify replacing z-stage and compensator subcomponents in the work performed section of the service tickets.
> 1: def classify_m3_replaced( ):
> 2: print('Classifying m3 replacement.')
> 3: training_data=data_processed.copy( ) #preprocessed data
> 4: training_data['label_code']=0
> 5: for index, row in training_data.iterrows( ):
> 6: work=row['WorkPerformed']
> 7: sentenceList=[x.strip( ) for x in work.split('.')]
> 8: for sentence in sentenceList:
> 9: if 'replace' in sentence and 'm3' in sentence:
> 10: training_data.at[index,'label_code']=1
> 11: if 'replace' in sentence and 'mirror' in sentence:
> 12: training_data.at[index,'label_code']=1
> 13: if 'change' in sentence and 'm3' in sentence:
> 14: training_data.at[index, 'label_code']=1
> 15: if 'order' in sentence and 'm3' in sentence:
> 16: training_data.at[index, 'label_code']=1
> 17: if 'install' in sentence and 'm3' in sentence:
> 18: training_data.at[index, 'label_code']=1
> 19: training_data.to_csv(output_path)

The "classify_m3_replaced" method receives preprocessed text strings at line 3 as shown above. The method parses the text string in a loop starting at line 5. Rules are applied at lines 9, 11, 13, 15, and 17. For example at line 9, the logic checks if there is a "replace" and "m3" in the text string. If the condition is true, meaning both these terms are present in the text string, a label "1" is assigned to the training data example. The method presented above assigns a "true" (or "1") label to the training data example if any one of the rules at lines 9, 11, 13, 15, and 17 is true. If none of the rules are evaluated as "true", the training data is labeled as "false" (or "0"). As this method is testing for M3 subcomponent, a "true" label means the work performed by service technician included replacing or servicing M3 subcomponent. The system can include similar methods for z-stage and compensator subcomponents. Therefore, the training data example can be assigned one or more subcomponent labels using the "true" outputs from the corresponding methods.

> Step 6 is the output step that includes assigning one or more labels of subcomponents that are determined using the rule-based algorithm described above.

Time Series Preprocessors

The sequencing instruments can generate primary metrics including focus scores and intensity values for multiple signal channels. Time series data from multiple signal channels are preprocessed to prepare training data for the classifier. It is challenging to identify features in time series data related to specific subcomponent failure. The technology disclosed was developed using graphical representations of time series data to identify features that can isolate a subcomponent causing failure. Two types of time series data are plotted, focus score and image intensity.

The focus score is defined as the average full width of clusters of molecules at half maximum (FWHM) representing their approximate size in pixels. In one instance, the minimum contrast and maximum contrast values are at the $10^{th}$ and $99.5^{th}$ percentiles per channel of selected columns of the raw image, respectively. Minimum contrast values can be at $15^{th}$ percentile or at the $5^{th}$ percentile. Similarly, maximum contrast values can be at the $90^{th}$ percentile or $95^{th}$ percentile. A selected column can be a specific tile or a lane of the flow cell. The process of determining an intensity value for each cluster in the template for a given sequencing image is referred to as intensity extraction. To extract intensity, a background is computed for a cluster using a portion of the image containing the cluster. The signal for the background is subtracted from the signal for the cluster to determine the intensity.

We present details of four programmatic detectors that can calculate the features used to isolate subcomponents causing malfunction.

Discontinuity Detector

The discontinuity detector identifies big jumps between successive cycles, for instance, in focus scores. Discontinuities in focus scores times series can indicate failure of z-stage subcomponent to adjust position the objective lens from tile to tile on the surface of flow cell which may not be optically flat. A faulty z-stage subcomponent can result in incorrect focus of image tiles resulting in discontinuities (or jumps) in the focus scores time series for multiple signal channels. The discontinuity detector detects jumps in focus scores time series which can indicate failure of a z-stage subcomponent. It has been observed that a faulty z-stage component can cause more discontinuities in focus scores time series of top surface of flow cell as compared to bottom surface of the flow cell. As a result, the time series of corresponding signal channels from the two surfaces may not follow a similar signal pattern thus lacking expected correlation.

Figure 4A:
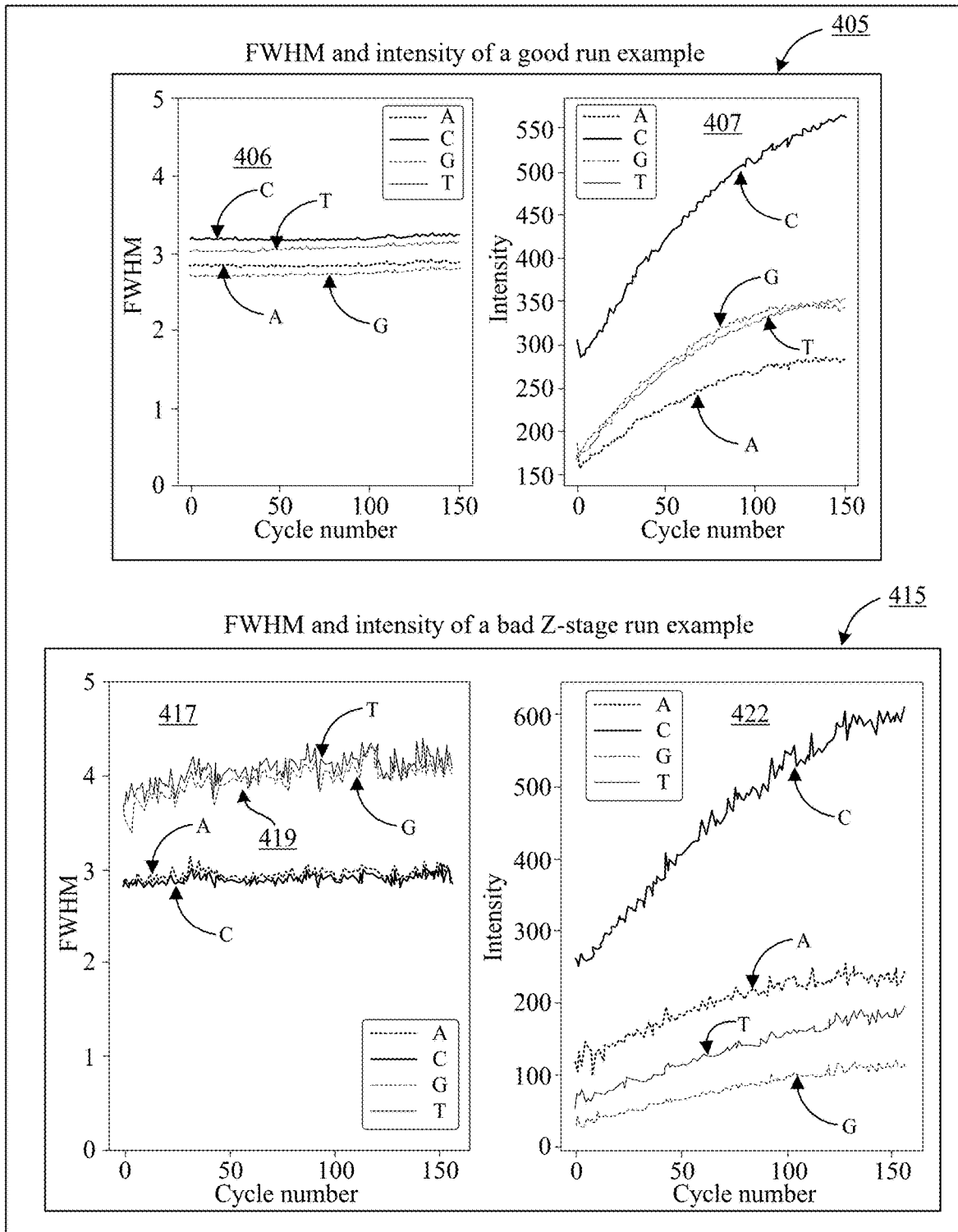
FIG. 4A presents examples of time series from a good sequencing run and examples of time series with discontinuities.

FIG. 4A presents a graphical illustration 405 showing focus scores time series 406 and image intensity time series 407 for a good sequencing run. The focus scores and intensity values are plotted for cycles (along x-axis) of the sequencing run. As mentioned above some sequencing runs can have two reads from opposite ends. In such case, the time series for two reads can be plotted separately or together in one graph. Separate focus score and intensity value time series are plotted for A, C, T, and G signal channels. In a good sequencing cycle, the focus scores for the four signal channels are smooth and the focus score values are between 2.5 and 3.5 (graph 406). Intensity values time series gradually increase from the start of the sequencing run at around 150 for A, G, T signal channels and around 300 for C signal channel. The intensities taper off towards the end of the sequencing run. The focus scores and image intensity time series for a good sequencing run do not have large variations or big jumps.

An illustration 415 presents time series data for focus scores (graph 417) and image intensity (graph 422) when for sequencing run with z-stage subcomponent malfunction. The focus scores time series for G and T signal channels shows discontinuities or big jumps (graphs 419). The discontinuity detector can calculate magnitudes of differences between focus scores at successive cycles in the focus scores time series per image channel in the sequencing run. The focus scores time series can be smoothed prior to calculation of the differences. The discontinuity detector includes logic to detect a number of successive cycles where the magnitudes of differences between successive cycles exceeds a predefined threshold. This calculated feature can be used as one of the input features in training data to train the fault detection classifier to detect abnormal signal channels. Expert fault isolation rules can check this calculated feature along with other condition to isolate a z-stage subcomponent as cause of a system malfunction.

The discontinuity detect can calculate "big jump" features for focus scores time series for a signal channel using the following "big_jump" method. The method calculates differences between a point in the focus scores time series for a channel and a previous point and compares the difference with a threshold. The threshold can be a magnitude or positive and negative difference values. As positive and negative differences, an example threshold pair is two positive standard deviations or one negative standard deviation in difference. Other threshold values can be set greater than or less than the example thresholds value mentioned above. As magnitude, an example threshold value is two standard deviations. Other threshold values greater than or less than two standard deviations can be used. Two calculated features num_fs_max_bigJump and num_fs_min_bigJump are stored in the calculated features database for training the fault detection classifier. In the big jump method presented below, comments are included for each line of code starting with '#' symbol describing the logic implemented in the line. Lines are numbered using a line number followed by a colon ":" symbol.

Big Jump Method

```
1: measures=focus_scores #Store focus scores for a signal
   channel in a list data structure
2: std=std(measures) #Calculate standard deviation for
   the time series
3: diffs=diff(measures) #Find difference between each
   point and previous point in time series
4: max_indexes=np.where(diffs>2*std) #identify indices
   where difference is greater than 2×std
5: min_indexes=np.where(diffs<=-std) #identify indices
   where difference is less than -1×std
6: channel+"_num_fs_max_bigump"=len(measures)/
   length(max_indexes) #divide the total
7: number of data points in focus scores time series by the
   count of max_indexes
8: channel+"_num_fs_min_bigJump"=len(measures)/
   length(min_indexes) #divide the total
9: number of data points in focus scores time series by the
   count of min_indexes
```

Figure 4B:
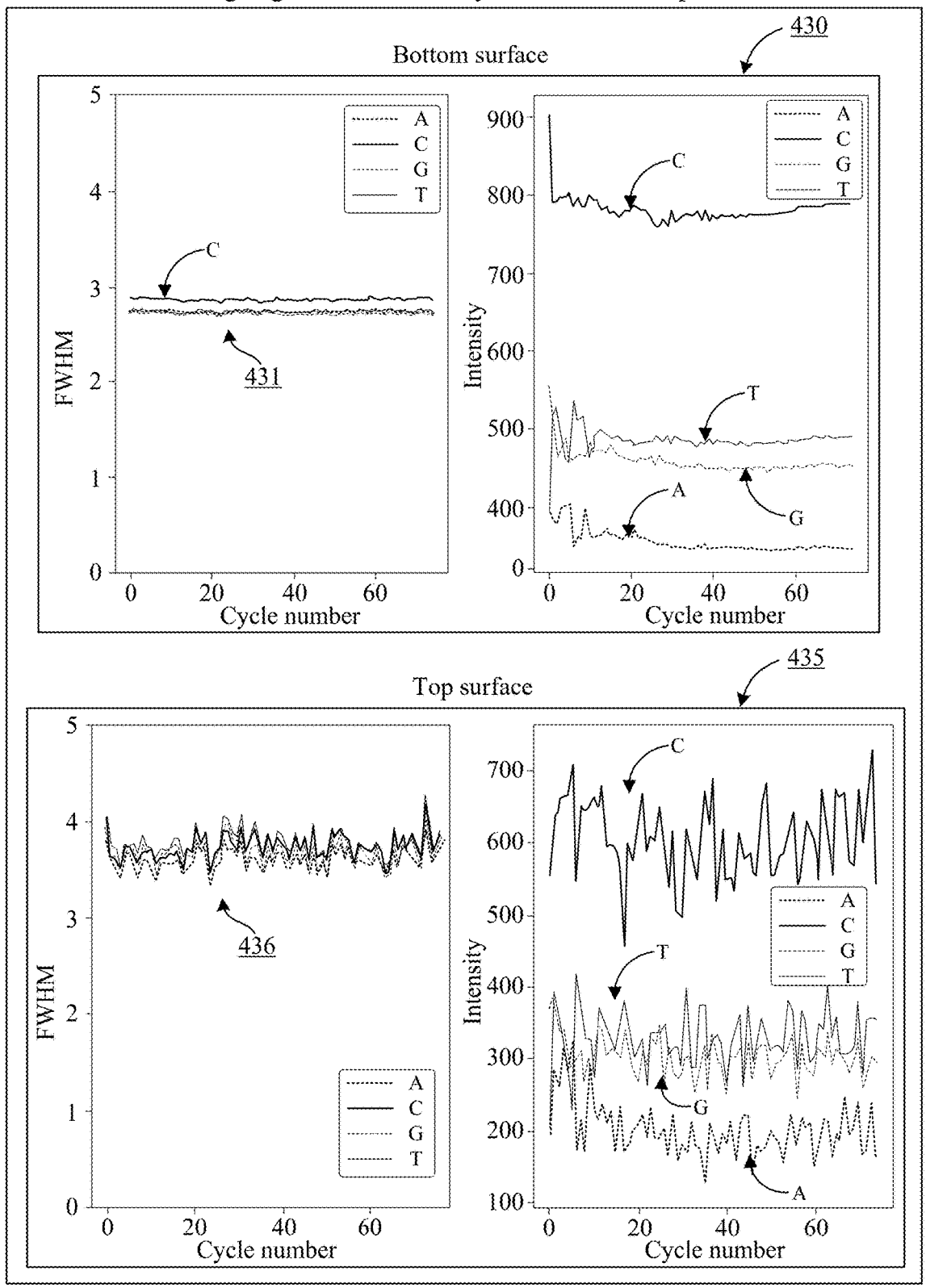
FIGS. 4B and 4C present examples of time series for top and bottom surfaces of a flow cell illustrating discontinuities, lack of expected correlation and trends.

FIG. 4B presents time series for bottom and top surfaces of a flow cell for all signal channels. For the bottom surface (graph 430), the focus scores time series for A, C, G, and T signal channels (labeled as 431) appear normal within 2.5 and 3.5 range and no large discontinuities are present in the signal channels. For the top surface (graph 435), the focus scores time series for A, C, G, and T signal channels (labeled as 436) appear abnormal with large discontinuities or big jumps. The values of data points in the time series are also higher than a normal range (2.5 to 3.5) indicating poor focus quality. It has been observed that a faulty z-stage component can cause more discontinuities in focus scores time series of top surface of flow cell as compared to bottom surface of the flow cell. The expert fault isolation rules can use check these conditions isolate z-stage subcomponent malfunction as a possible cause of system failure.

Drift Detector

The drift detector compares drift over time in signals captured by cameras on different optical paths, in order to isolate malfunctioning of a component present in one optical path but not the other. In some sequencing system the M3 mirror subcomponent is positioned on one optical leg and not the other, therefore features calculated from drift detector can identify an M3 subcomponent failure. When M3 subcomponent malfunctions, images from both red and green actuations of one camera suffer a focus score of FWHM degradation relative to the other camera.

Figure 4C:
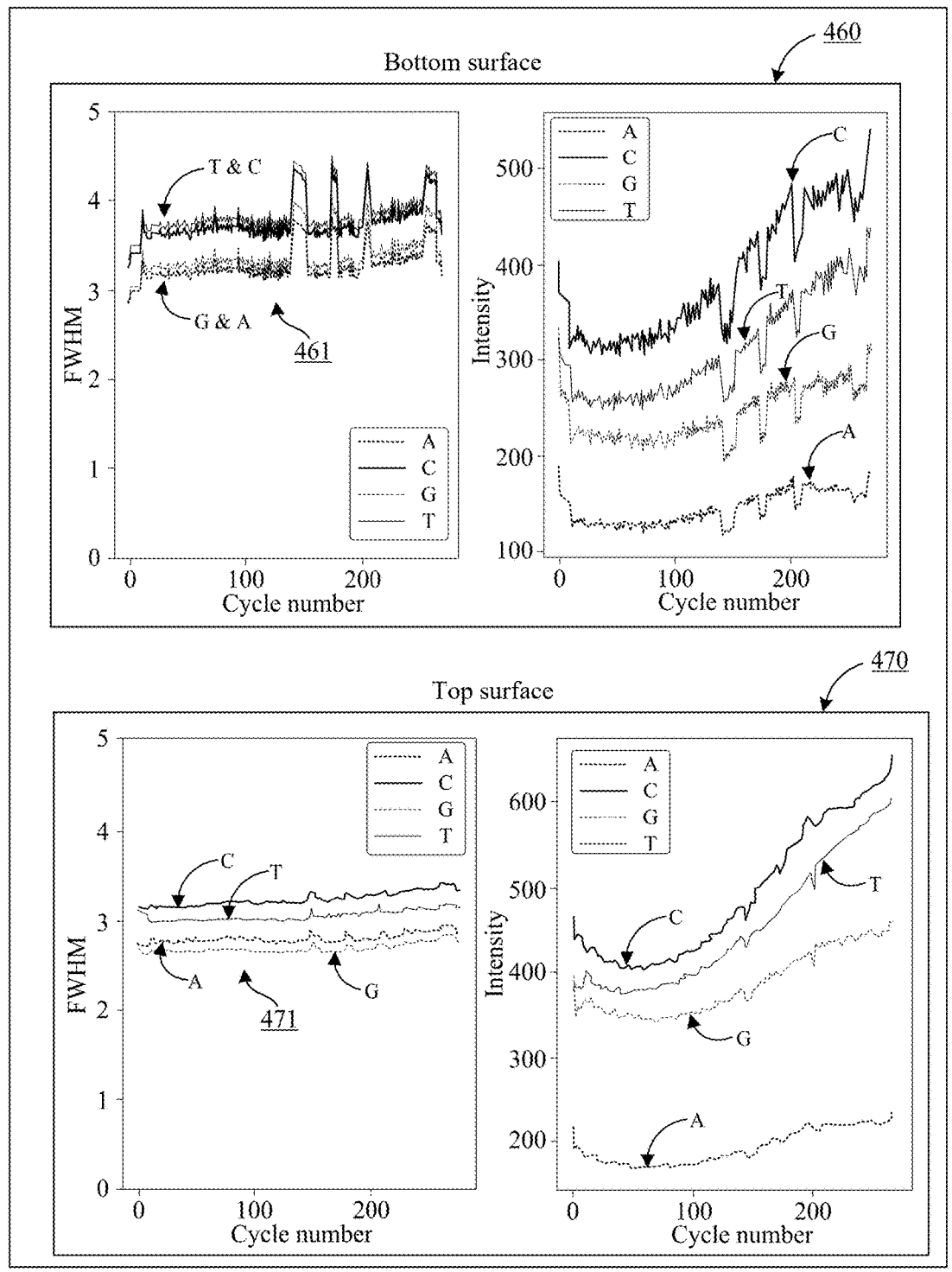
Figure 4D:
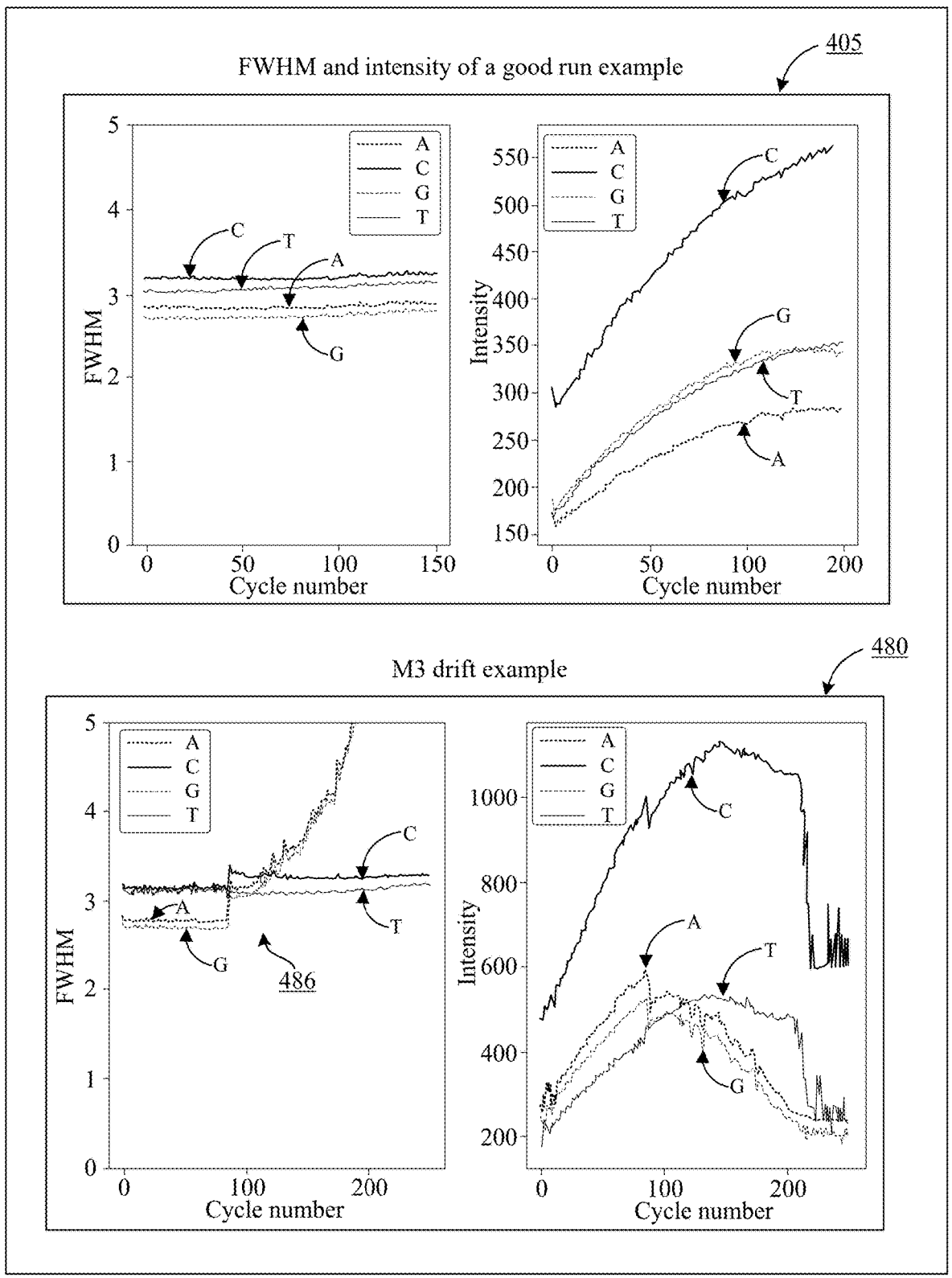
FIG. 4D presents examples of time series illustrating pairs of signal channels drifting apart, indicating failure of M3 subcomponent.

FIG. 4D presents an example of drift caused by M3 subcomponent malfunction. The illustration 480 presents graphical plot of focus scores time series 486 for four signal channels. The two signal channels A and G detected by camera S2 drift together in close proximity to each other. Similarly, the C and T signal channels detected by camera S1 drift together following a similar signal pattern. This situation can indicate a possible M3 subcomponent failure. The M3 detector can implement logic to capture the signal channel drift phenomenon. In one implementation, the M3 drift method presented below detects drifting of two signal time series from one camera.

M3 Drift Method

```
#Applying smoothing filter
1: a_np=smooth(A_read[0].focus_scores)
2: c_np=smooth(C_read[0].focus_scores)
3: g_np=smooth(G_read[0].focus_scores)
4: t_np=smooth(T_read[0].focus_scores)
#Calculating difference of each cycle with the same cycle
   in another channel
5: ac_diff_abs=absolute(subtract(a_np, c_np))
6: gt.diff_abs=absolute(subtract(g_np, t_np))
7: ag_diff_abs=absolute(subtract(a_np, g_np))
8: ct_diff_abs=absolute(subtract(c_np, t_np))
#Dividing time series to two portions (we want to see if
   the second half of the signals are drifting from the first
   half)
9: window=round(length(A_read[0].focus_scores)/2)
#Calculating average value of the difference between
   second half and first half
10: dif_mean_ac=absolute(mean(ac_diff_abs[win-
   dow:])-mean(ac_diff_abs[:window]))
11: dif_mean_ag=absolute(mean(ag_diff_abs[window:])-
   mean(ag_diff_abs[:window]))
12: dif_mean_ct=absolute(mean(ct_diff_abs[window:])-
   mean(ct_diff_abs[:window]))
13: dif_mean_gt=absolute(mean(gt_diff_abs[window:])-
   mean(gt_diff_abs[:window]))
#If (A and G) or (T and C) are drifting together it is M3
   drift
14: if dif_mean_ac>dif_mean_ag and
   dif_mean_gt>dif_mean_ct:
#Other values of threshold can be set as more examples of
   M3 drift are analyzed
15: if dif_mean_ac>0.2:
16: num_of_drifts=num_of_drifts+1
17: if dif_mean_gt>0.2:
18: num_of_drifts=num_of_drifts+1
19: if num_of_drifts==2:
20: return True
21: else: return False
```

In a first block of M3 drift method (lines 1 to 4) a smoothing filter is applied (such as Savgol filter, Moving Average filter, Kernel Smoother, etc.) to remove noise.

In a second block of M3 drift method (lines 5 to 8) difference between focus score values of pairs of signal channels. The pairs for which difference is calculated are selected using camera pair channels and LED pair channels. For example, pairs AC and GT are based on the same LED source. Red LED source excites dyes to detect A and C signal channels and green LED source excites dyes detect G and T signal channels. Signal channel pairs AG and CT are based on detection by the same camera. FIG. 2A illustrates that C and T signals are detected by camera S1 and A and G signals are detected by camera S2. The difference between these pairs of signal channels can help identify possible drift of channels. If a pair of signal channels from a same camera is drifting, then it can identify possible M3 issue as M3 subcomponent is present in the optical path of one camera (S1) and not the other camera (S2).

In a third block of M3 drift method (line 9), the focus scores time series is partitioned into two portions (or windows) to compare the focus scores in a second portion with the first portion to detect drift.

In a fourth block of M3 drift method (lines 10 to 13), average difference between first half and second half of the four pairs of signal channels presented above (second block) is calculated.

In a fifth block of the M3 drift method (lines 14 to 20), the average differences between pairs of signal channels are compared. The two camera pair channels (AG and CT) are compared with two LED pair channels (AC and GT) to check if the differences in camera pair signal channels are less than LED pair signal channels (line 14). If this condition is true, then average difference of each LED pair AC and GT is compared with a threshold (0.2) at lines 15 and 17, respectively to make sure that they are above 0.2. The threshold value can be set above or below 0.2 based on analysis of more M3 failure examples in sequencing instruments. If both conditions are true, then two counters are incremented at lines 16 and 19, respectively. If the counter becomes 2 (line 19) then M3 method returns "true" (line 20) which means that M3 drift is present in the observed signal channels. Otherwise, the method returns "false" at line 21. The calculated M3 drift feature can be stored in calculated features database 116.

Surface-to-Surface Correlation Detector

The surface-to-surface correlation detector detects whether signal channels for a top surface of the flow cell follow a similar signal pattern to corresponding signal channels for a bottom surface of the flow cell. When the optical subsystem components are working normally, the corresponding signal channels for top and bottom surfaces follow a similar signal pattern. Failure of optical system subcomponents can cause variation in signal channel pattern between the top and bottom surfaces.

FIG. 4B shows focus scores time series 431 for signal channels from bottom surface and focus scores time series 436 for corresponding signal channels from top surface of a flow cell. The multiple time series from top surface include discontinuities or big jumps while corresponding multiple time series from bottom surface are smooth. The surface-to-surface correlation detector can calculate statistical correlation using for example, Pearson correlation coefficient. The correlation coefficient can range from −1 to 1. Correlation coefficient values closer to 1 indicate a higher correlation between time series of respective signal channels from two surfaces. A separate correlation coefficient is calculated for a channel between top and bottom surfaces. Therefore, surface-to-surface correlation detector can generate four calculated features, "A_correlation", "C_correlation", "G_correlation", and "T_correlation". The lack of expected correlation between abnormal signal channels 436 and normal signal channels 431 can indicate a z-stage or compensator subcomponent failure. The calculated features can be stored in calculated features database 116.

FIG. 4C includes time series for four signal channels from a bottom surface (460) and a top surface (470) of a flow cell. In this example, the focus scores time series 461 from bottom surface have discontinuities while corresponding signal channels 471 from top surface are within the 2.5 to 3.5 range indicating good focus quality. The surface-to-surface correlation detector can calculate the correlation coefficient values for the four signal channels. Expert fault isolation rules can check if all signal channels from the bottom surface are abnormal and at least a few signal channels from the top surface are normal. These two conditions can indicate a possible compensator subcomponent malfunction.

Trend Detector

The trend detector can identify degrading focus when the focus score values in a last part of the focus scores time series is higher than focus score values in a first part of the focus scores time series. For example, the focus scores times series 436 (in FIG. 4B) for signal channels from a top surface have relatively higher focus score values in a last part of the time series as compared to a first part of the time series. In one implementation, the trend detector can calculate the trend using the logic presented in the following trend detection method.

Trend Detection Method
1: first_mean=average value of the first window
2: last_mean=average value of the last window
3: slope=(last_mean−first_mean)/(len(focus_scores)−2*window_size)

The focus scores time series per signal channel is divided into ten windows. The size of the window is equal to the number of focus score values in a window. Less than ten or greater than ten windows can be used for partitioning the focus scores time series. The trend detection method calculates two averages for focus scores time series. The first average (line 1) is for a first window of the time series and a second average (line 2) is for a last window of the focus scores time series. It is understood that other windows (or partitions) of the time series data can be used to determine the first mean and the last mean. For example, the average value of the second window can be used to determine "first_mean" in line 1 of trend detection method and the average value of the second last window can be used to determine "last_mean" in line 2 of the trend detection method. Data from other windows can be used to calculate "first_mean" and the "last mean" values.

At line 3 of the trend detection method, a ratio is calculated between the difference of the last window's average and the first window's average to number of focus score values between the first and last window. Higher values of slope can indicate the signal trend with an increasing value of focus score indicating focus degradation towards the end of the sequencing run. The slope features for four focus scores time per surface for a read (A_fs_delta_slope, C_fs_delta_slope, G_fs_delta_slope, T_fs_delta_slope) are stored in calculated features database 116.

The primary metrics and calculated features can be fed to a fault detection classifier to classify signal channels as normal or abnormal. We present training of an example fault detection classifier and application of the trained classifier to classify production time series data.

Mid-Process Vibration Detector

Figure 4E:
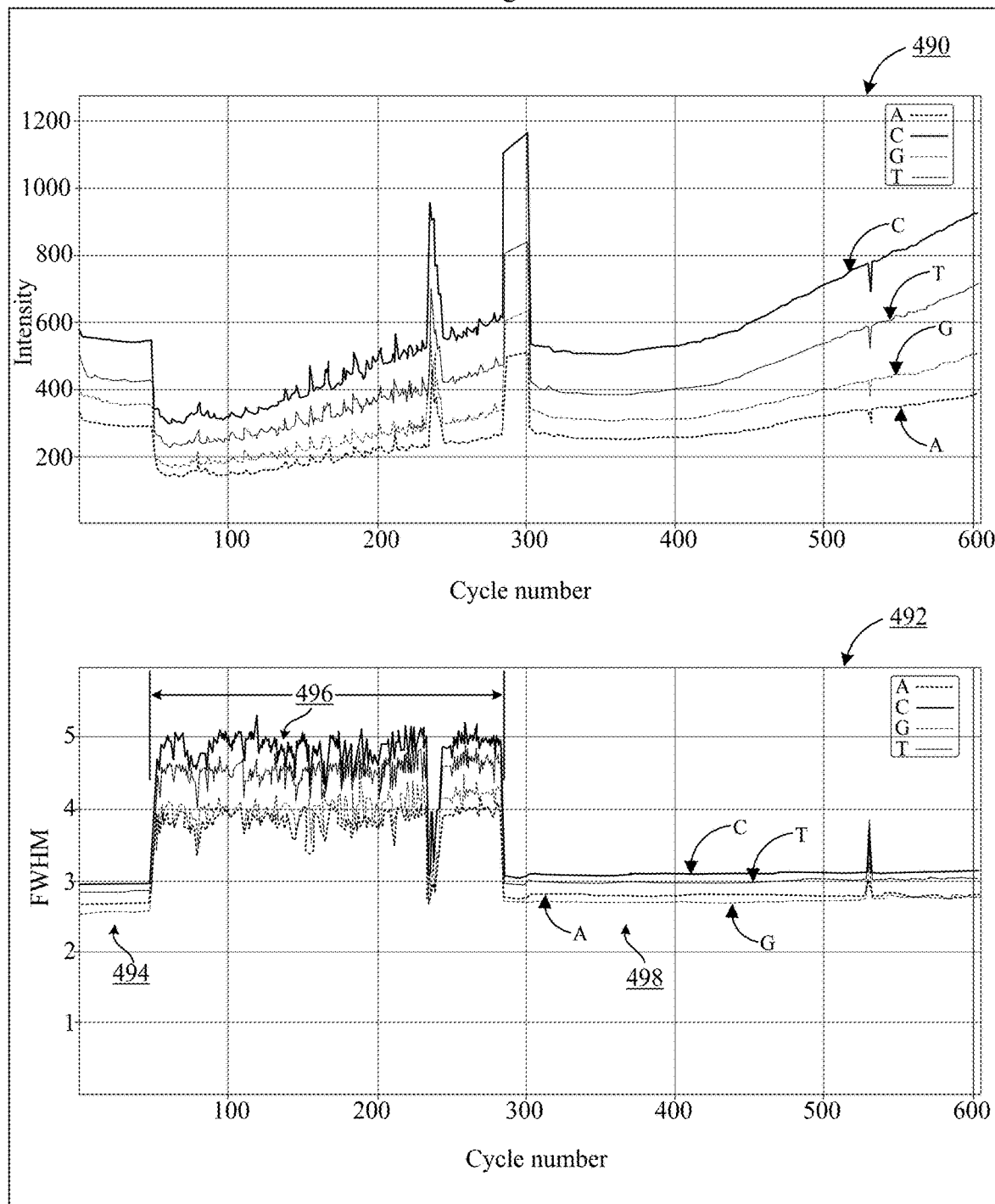
FIG. 4E presents an example time series illustrating signal channels with mid-process vibration feature due to z-stage subcomponent malfunction.

The mid-process vibration detector includes logic to process focus scores (FWHM) time series from at least one signal channel for a read and identify a signal channel that is normal in a first part and a last part but includes erratic spikes with higher average focus scores (or FWHM) in between the two normal or good parts. For example, FIG. 4E shows intensity values time series 490 (top) and focus scores time series 492 (bottom) for signal channels from a sequencing instrument. The focus scores time series includes two goods part 494 and 498 at the beginning and end of the sequencing read. However, the middle part 496 shows discontinuities (or spikes) in all four signal channels. This mid-process vibration feature in focus scores time series illustrates a z-stage problem that can be caused by tight engagement of lockout screws that are used to secure z-stage subcomponent. We present an example mid-process vibration detection method below followed by an explanation of the method.

Mid-Process Vibration Detection Method

```
 1: def is_the_jump(measures, std):
 2: diffs=np.diff(measures)
 3: max_indexes=np.where(diffs>std)
 4: min_indexes=np.where(diffs<=std)
 5: if (len(max_indexes[0])==0) or (len(min_indexes[0])
    ==0):
 6: return False
 7: firs_max=max_indexes[0][0]
 8: #first good part
 9: good_part=measures[0:firs_max]
10: if len(good_part)==0:
11: return False
12: good_avg=sum(good_part)/len(good_part)
13: #middle bad part
14: bad_part=measures[max_indexes[0][0]:min_indexes
    [0][-1]] #first max 15: till lost min (first rise till last fall
16: if len(bad_part)==0:
17: return False 18: bad_avg=sum(bad_part)/len(bad_
    part)
19: #last good part
20: good_part2=measures[min_indexes[0][-1]:-1] #last
    fall till end
21: if len(good_part2)==0:
22: return False 23: good_avg2=sum(good_part2)/len
    (good_part2)
24: if (bad_avg-good_avg)>0.1 and (bad_avg-goo-
    d_avg2)>0.1:
25: print(str(bad_avg-good_avg)+","+str(bad_avg-goo-
    d_avg2))
26: return True
```

The "is_the_jump" method presented above can detect mid-process vibration in focus scores time series as shown in FIG. 4E. The method receives focus scores time series (as "measures" parameter) and a standard deviation (as "std" parameter) in line 1 of the method as presented above. At line 2, the method calculates "diffs" which are difference between focus scores of successive cycles in a read. At lines 3 and 4, the method determines indices of elements in the "diffs" data structure where the value of the difference between successive cycles is above a threshold such as one standard deviation. Other values of threshold can be used greater than one standard deviation. The threshold can be a magnitude or positive and negative difference values. As positive and negative differences, an example threshold pair is one positive standard deviation or one negative standard deviation in difference. At lines 5 and 6, the results in the "max_indexes" and "min_indexes" data structures are checked to see if these are not empty. If either one of the two data structures is empty, the method returns a "false" output indicating that the time series does not contain mid-process vibration feature.

The method includes logic to detect a first element in the time series where the jump occurs. This element can be a first data point (or one of the first three or five data points) in the time series at the beginning of the middle part illustrated as 496 in the time series in FIG. 4E. The method stores the index of the first data point as "firs_max" at line 7. The method stores the part of the time series before the "firs_max" as "good_part" at line 9. The good part represents the first part of the time series indicated by the label 494. The average of data points in the first good part is calculated at line 12 and saved in "good_ave" variable.

The method detects a bad part of the time series at line 14 which corresponds to the time series part labeled as 496 in FIG. 4E. A "bad_avg" variable stores average focus score in the bad part of the time series at line 18.

The method detects the second good part of the time series in line 20. The second good part of the time series is labeled as 498 in FIG. 4E. The average of the second good part is stored in "good_avg2" variable at line 23.

The method compares difference between the bad average and the two good averages at line 24. If the difference between the bad average and the good averages is greater than "0.1" for both first and second good parts then the method returns "true" which indicates that the time series contains mid-process vibration feature. Other values of threshold greater than or less than "0.1" can be used to compare the averages at line 24. The presence of mid-process vibration feature in focus scores time series can indicate a z-stage failure. The result from the above-described method can be evaluated by an expert rule. If the method returns "true", the expert rule can generate an alert for z-stage subcomponent malfunction. The expert rule can also present an explanation of the alert, such as, "z-stage malfunction caused by tight engagement of lockout screws."

Fault Detection Classifier

The technology disclosed applies a fault detection classifier and expert fault isolation rules in stages. A classifier is applied in a first stage to classify a time series of a signal channel as normal or abnormal. Abnormal classification of a signal channel can indicate a serviceable fault and is further processed against hand crafted expert rule sets to isolate the subcomponent causing malfunction. Random forest is one example of a classifier applied to classify the signal channels. Other examples of classifiers that can be applied for fault detection include decision tree classifier, eXtreme gradient boosting (XGBoost) classifier, gradient boosted decision trees (GBDT) classifier, AdaBoost classifier, etc. In other implementation, classifiers such as support vector machines (SVM), logistic regression, etc. can also be applied. With a large, labeled training data set, deep neural networks can also be applied for fault detection classification. In the following sections we present training of the random forest classifier and application of the trained model to production data.

Random forest classifier (also referred to as random decision forest) is an ensemble machine learning technique. Ensembled techniques or algorithms combine more than one technique of the same or different kind for classifying objects. The random forest classifier consists of multiple decision trees that operate as an ensemble. Each individual decision tree in random forest acts as base classifier and outputs a class prediction. The class with the most votes becomes the random forest model's prediction. The fundamental concept behind random forests is that a large number of relatively uncorrelated models (decision trees) operating as a committee will outperform any of the individual constituent models.

Classifier Training Architecture

Figure 5A:
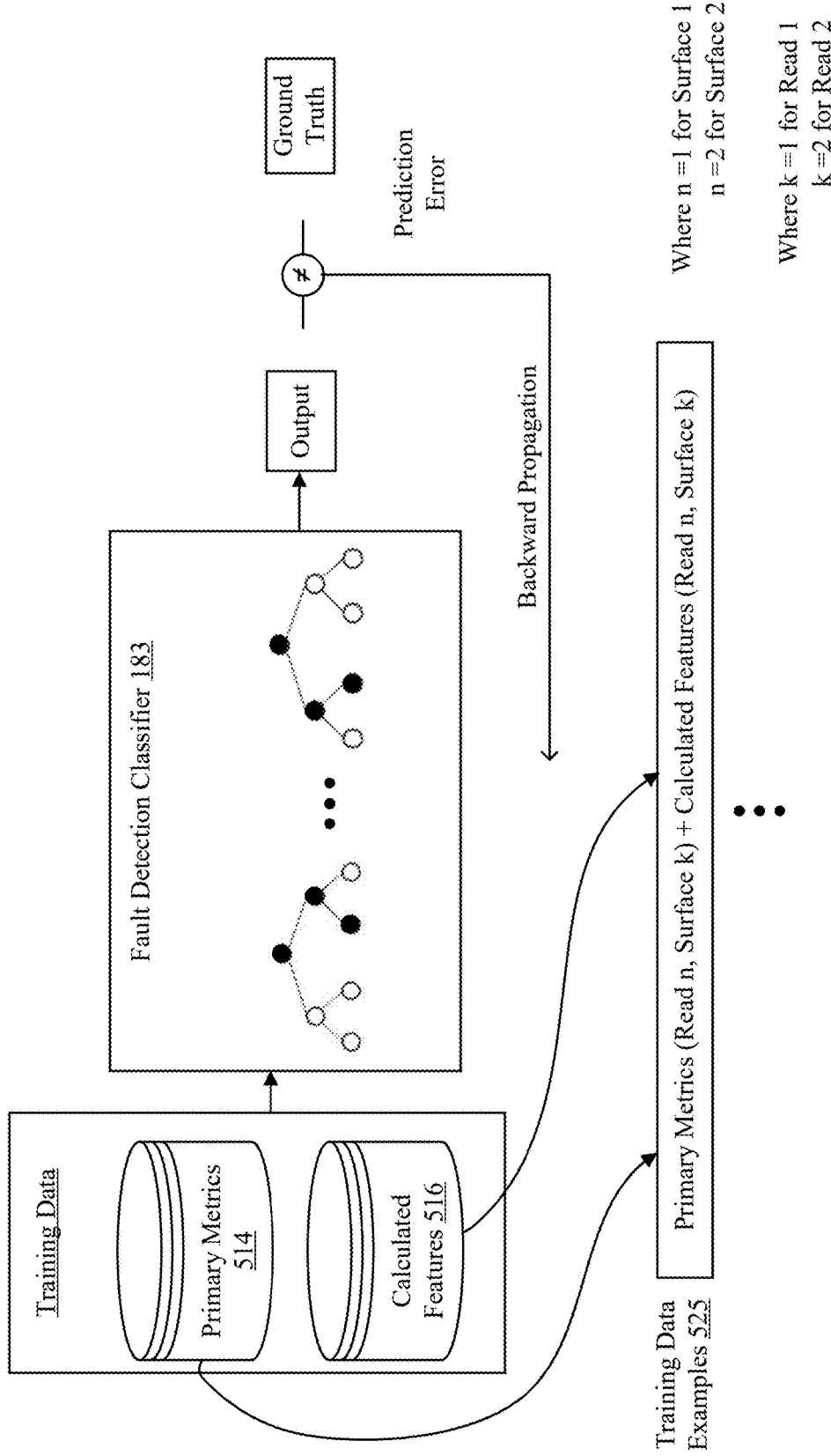
FIG. 5A presents training of a fault detection classifier using labeled training data comprising primary metrics and calculated features.

FIG. 5A presents an example training architecture for fault detection classifier 183. The training data comprises of time series of signal channels from sequencing runs. The training data includes primary metrics 514 and calculated features 516. An example 525 in the training data includes primary metrics and calculated features from one read per surface of the flow cell. There can be two reads per sequencing run and a flow cell can have two surfaces containing samples, therefore, there can be up to four examples (or rows) of training data per sequencing run. Sequencing runs can have fewer than four rows if the run was stopped before completion or data is collected for one read. Ground truth training data is prepared by first cleaning the data and then applying label. Training data can be cleaned by applying smoothing filter to remove noise. For example, Savgol (Savitzky-Golay) filter can be applied to time series data points for smoothing the data, i.e., to increase the precision of the data without distorting the signal tendency. Time series data examples are labeled as normal (labeled as "0") or abnormal (labeled as "1"). The labeling is performed by reviewing the time series graphs as shown in FIGS. 4A to 4C and identifying the subcomponent failures.

In one instance the model was trained using about 300 labeled training data examples. The size of the training data is increasing as more failure data is collected from user of the sequencing systems. We now present examples of input features for training the classifier. The input features include primary metrics and calculated features.

The primary metrics in the primary metrics database 514 can include the following data. The training data example 525 is broken down in smaller tables labeled as "1" through "12" in FIGS. 5B, 5C, and 5D. Primary metrics are provided by the instrument. FIGS. 5B, 5C and 5D present an example 525 of data values for the primary metrics and calculated features. In FIG. 5B, tables labeled "1", "2", and "3" present primary metrics and table labeled "4" presents calculated features. Headers of the tables present feature names, three data rows from example training data are shown in FIGS. 5B, 5C, and 5D for illustration purposes. We have listed the primary metrics below.

- surface identifier (1 or 2),
- read number (1 or 2),
- sequencing run start date and time,
- identifier of the sequencing run,
- serial number of the sequencing instrument,
- sequencing run state (completed or stopped),
- size of the data output by the sequencing instrument for a sequencing run (e.g., in bytes),
- Q30 quality score value,
- percentage of sequence aligned,
- error rate, refers to the percentage of bases called incorrectly and can be calculated from the reads that are aligned to PhiX control in the sample
- maximum number of cycles in the sequencing run,
- tile count indicating number of tiles imaged in the sequencing run,
- a concatenated string of identifier of sequencing run, read number and surface identifier The calculated features in the calculated features database 516 can include the following calculated features. FIGS. 5B (table 4), 5C (tables 5, 6, 7, 8), and 5D (tables 9, 10, 11, 12) present example values for calculated features. The top row in the tables lists feature names. Three example values for each calculated feature are shown. Examples of calculated features are listed below:

- average intensity for the read per surface,
- average focus score for the read per surface,
- volatility of intensity per signal channel calculated as absolute intensity value difference between each cycle (A_intensity_change; C_intensity_change; G_intensity_change; T_intensity_change),
- volatility of focus scores per channel calculated as absolute focus score difference between each cycle (A_fs_change; C_fs_change; G_fs_change; T_fs_change),
- slope feature per image channel calculated by partitioning focus scores time series in ten windows and comparing the focus score from the last window with the first window, slope feature can be calculated using trend detection method presented above (A_fs_delta slope; C_fs_delta slope; G_fs_delta slope; T_fs_delta_slope),
- two big jump features per signal channel identifying discontinuity in time series calculated by applying M3 drift method presented above, (A_num_fs_max_bigJump; A_num_fs_min_bigJump, C_num_fs_max_bigJump; C_num_fs_min_bigJump; G_igJump; G_num_fs_min_bigJump; T_num_fs_max_bigJump; T_num_fs_min_bigJump),
- correlation features calculated per channel using Pearson correlation coefficient, the correlation is calculated between focus scores time series for two surfaces per image channel (A_correlation; C_correlation; G_correlation; T_correlation)
- M3 drift feature (true or false) calculated using M3 drift method presented above,
- minimum and maximum focus score values per image channel per surface in a read (A_fs_min; A_fs_max; C_fs_min; C_fs_max; G_fs_min; G_fs_max; T_fs_min; T_fs_max),
- difference between maximum and minimum focus score values per image channel per surface in a read (A_fs_min_max_diff=A_fs_max−A_fs_min; C_fs_min_max_diff=C_fs_max−C_fs_min; G_fs_min_max_diff=G_fs_max−G_fs min; T_fs_min_max_diff=T_fs_max−T_s_min),
- focus scores differences between two surfaces by calculating difference between channel_fs_min_max_diff for respective channels (as calculated above) for two surfaces and taking an average, (channel=A, C, G, T)

The training data example 525 comprise input features including primary metrics and calculated feature values for one read per surface of a sequencing run. A random forest classifier with 100 decision trees and a depth of 12 worked well. It is understood that random forest classifiers with a range of 100 to 300 decision trees or 100 to 400 decisions trees and a range of depth from 10 to 20 or 8 to 22 is expected to provide good results for this implementation. The hyperparameters are tuned using randomized search cross-validation. Increasing the number of trees can increase the performance of the model however, it can also increase the time required for training.

Decision trees are prone to overfitting. To overcome this issue, bagging technique can be used to train the decision trees in random forest. Bagging is a combination of bootstrap and aggregation techniques. In bootstrap, during training, a sample of rows is taken from training database and used to train each decision tree in the random forest. For example, a subset of features for the selected rows can be used in training of decision tree 1. Therefore, the training data for decision tree 1 can be referred to as row sample 1 with column sample 1 or RS1+CS1. The columns or features can be selected randomly. The decision tree 2 and subsequent decision trees in the random forest are trained in a similar manner by using a subset of the training data. Note that the training data for decision trees is generated with replacement i.e., same row data can be used in training of multiple decision trees.

The second part of bagging technique is the aggregation part which is applied during production. Each decision tree outputs a classification for each class. In case of binary classification, it can be "1" indicating a bad signal channel or "0" indicating a good signal channel. The output of the random forest is the aggregation of outputs of decision trees in the random forest with a majority vote selected as the output of the random forest. By using votes from multiple decision trees, a random forest reduces high variance in results of decision trees, thus resulting in good prediction results. By using row and column sampling to train individual decision trees, each decision tree becomes an expert with respect to training records with selected features.

During training, the output of the random forest is compared with ground truth labels and a prediction error is calculated. During backward propagation, the model weights are adjusted so that the prediction error is reduced. The parameters (such as weights) of the trained random forest classifier are stored for use in fault detection classification of production signal channels during inference.

We now describe the classification of production signal channels from sequencing run using the trained fault detection classifier.

Classifier Production Architecture

Figure 5E:
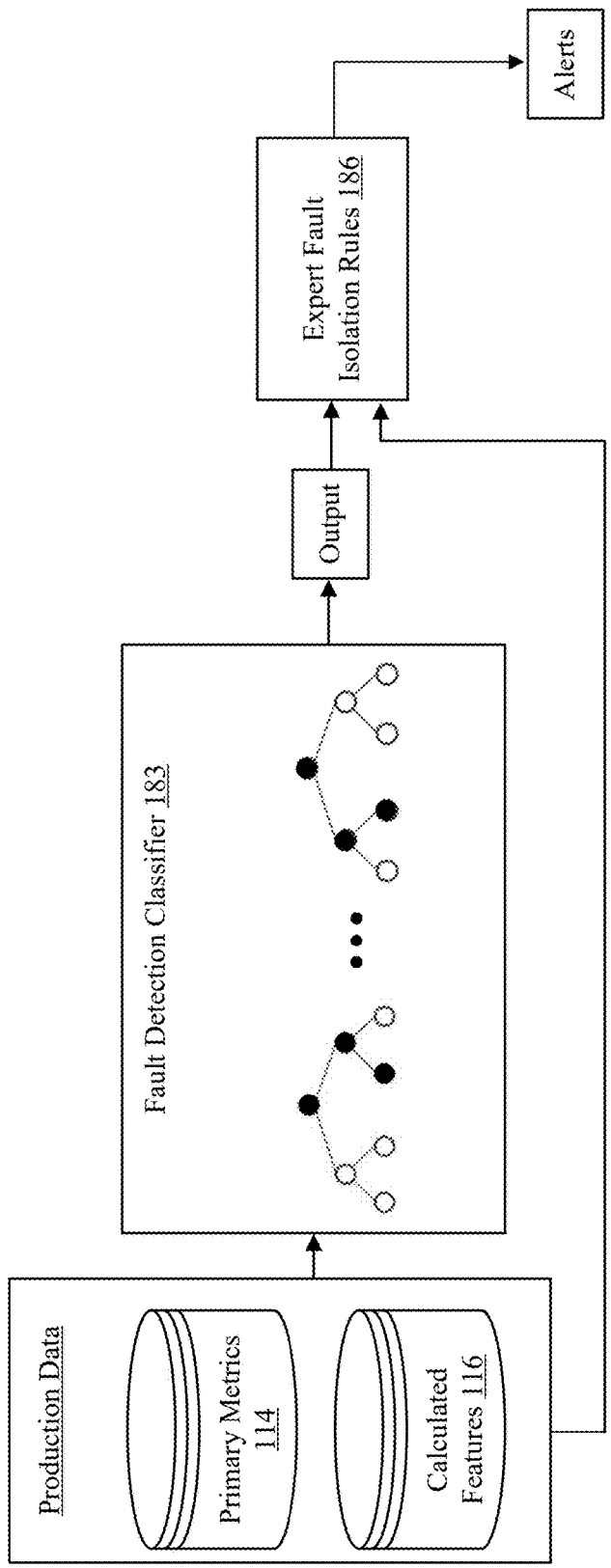
FIG. 5E presents two stage process of generating alerts including classification of production time series data using fault detection classifier and isolation of malfunctioning subcomponent using expert fault isolation rules.

FIG. 5E shows the two-stage classification of sequencing runs using a fault detection classifier 183 in a first stage and expert fault isolation rules 186 in a second stage. In the first stage the input to the fault detection classifier can include the primary metrics and calculated features as described above.

The fault detection classifier 183 classifies a signal channel (per read per surface) as normal or abnormal. The output from the classifier can include a normal/abnormal classification for a signal channel and a confidence score for the prediction. As there are four signal channels per surface, two surfaces per read, and two reads in a sequencing run, there can be 32 outputs (including output label and confidence score per label) from fault detection classifier per sequencing run (4 signal channels×2 surfaces×2 reads).

The classifications for signal channels are provided as input to expert fault isolation rules 186 along with calculated features 116. The input to the expert fault isolation rules can also include some primary metrics such as identifiers of the sequencing run, read number and surface number. The expert fault isolation rules suggest which subcomponent to replace and present reasoning embodied in the rule that is applied. We present details of the fault isolation rules in the following section.

Expert Fault Isolation Rules

Figure 6A:
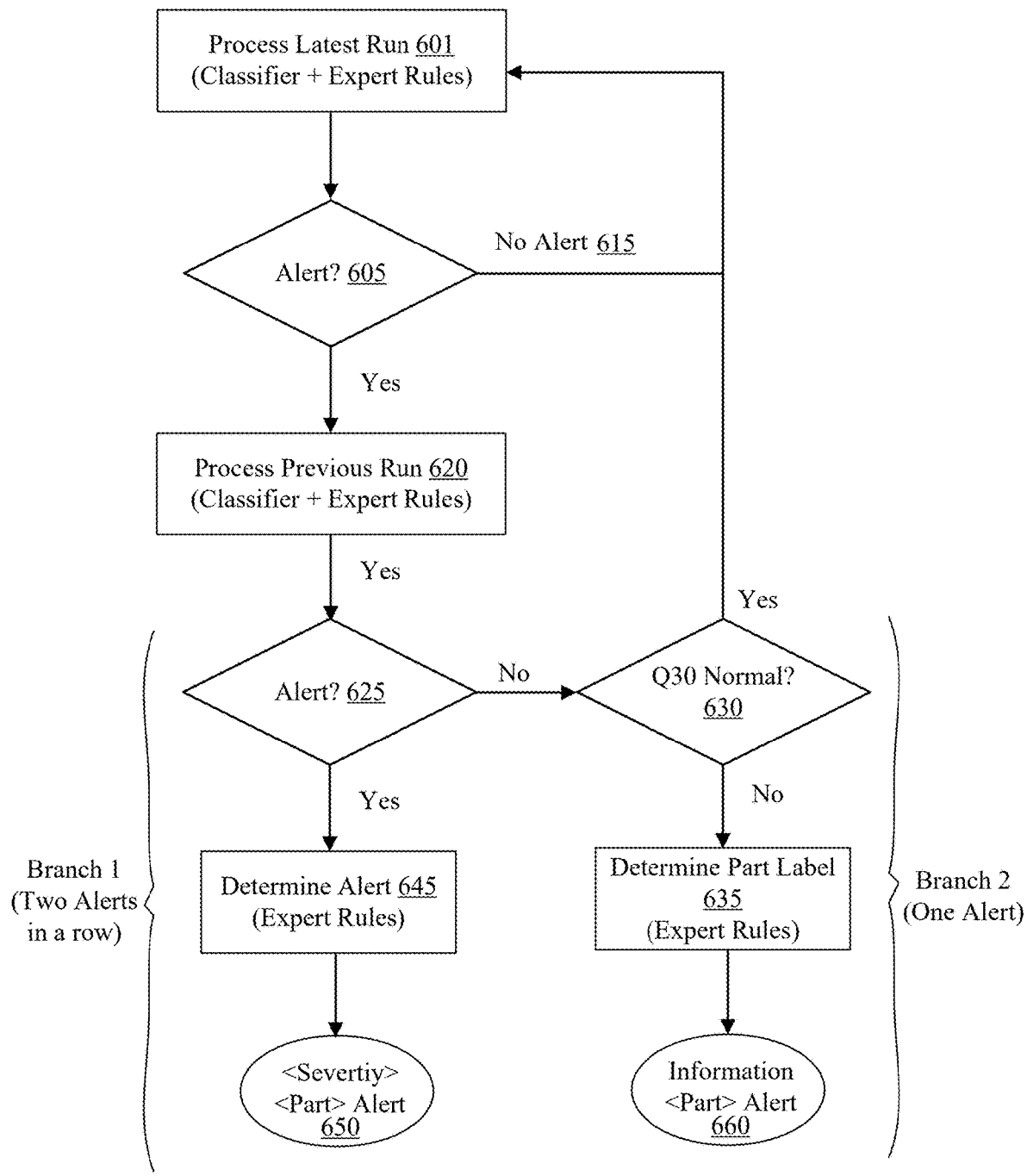
Figure 6B:
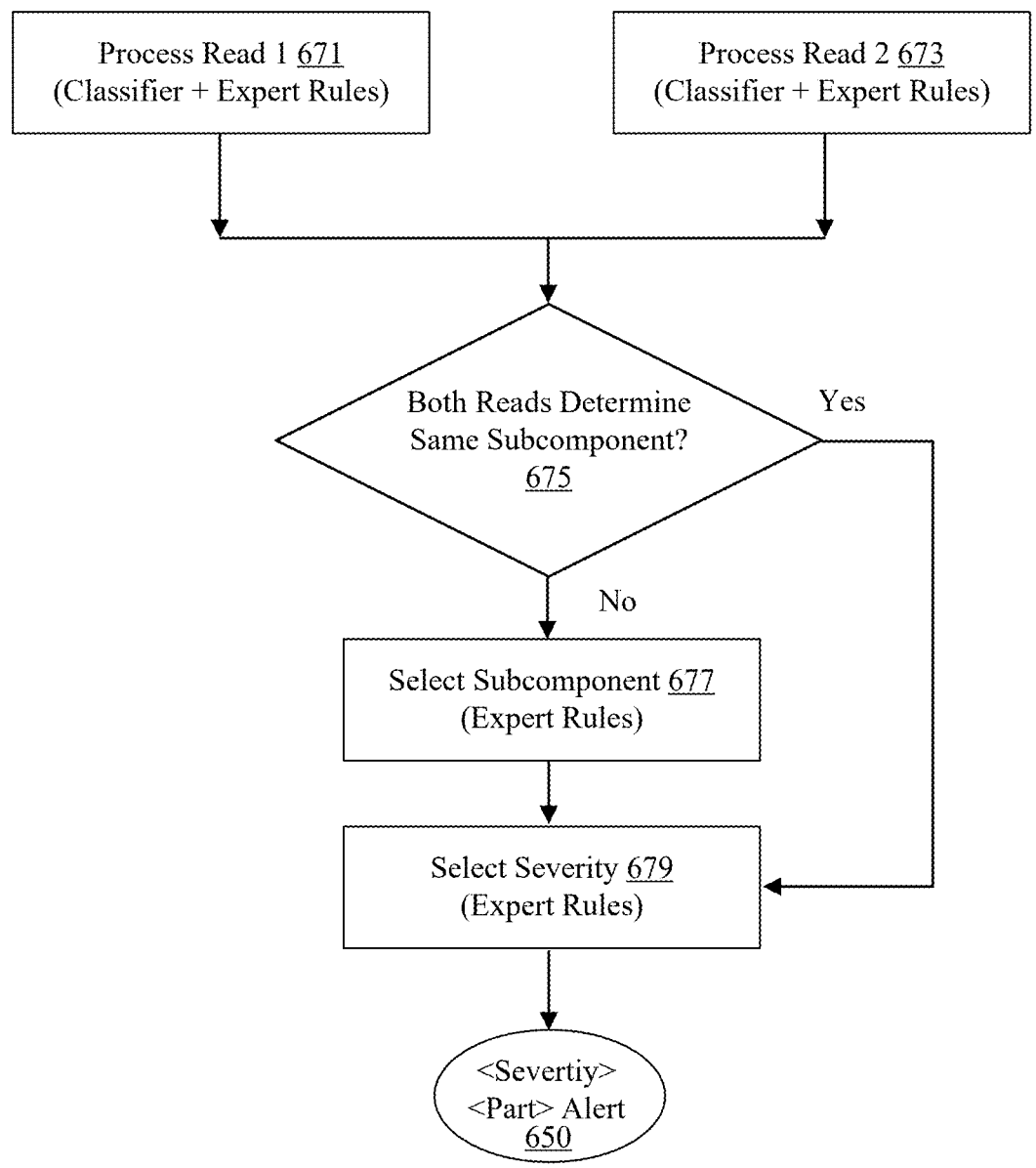

The classifications of signal channels are processed against hand crafted expert rule sets to isolate subcomponent causing malfunction. FIGS. 6A, 6B, and 6C present processing of classifications of multiple signal channel for one read (FIG. 6C), then combined across two reads in a run (FIG. 6B) and finally across multiple sequencing runs (FIG. 6A) to isolate a subcomponent causing failure.

FIG. 6A presents a high-level process flow chart for isolating subcomponent by processing multiple sequencing runs from a sequencing instrument. FIG. 6A presents the process at a sequencing run-level and is further refined in flowcharts in the following figures.

At a step 601, two-stage process of classification and application of expert rules is applied to a sequencing run. The system applies a trained classifier to multiple signal channels from a sequencing run. The results of the classification are further processed by expert fault isolation rules to isolate a subcomponent causing malfunction. At a step 605, the output from expert fault isolation rules is checked to see if an alert is generated or not. If no alert is detected at the step 605, then process can be repeated for a next sequencing run (615). If an alert is detected at the step 605, the process of step 601 is repeated for a previous sequencing run at a process step 620. In one implementation, immediately preceding sequencing run is evaluated at the step 620. In other implementations, sequencing runs earlier than immediately preceding sequencing run can be evaluated at a step 620. In a sequential process of the sequencing runs, the system can store results for processing alerts for a sequencing run in a memory or persistent data store and access the stored results for any of the previously processed sequencing runs to check if an alert was generated or not.

The decision step 625 can lead to two branches of the process step. A first branch (branch 1) is followed when an alert is not detected at a step 625. This can indicate two alerts in a row for two sequencing runs. A second branch (branch 2) is followed if an alert is not detected at a step 625. The first time an alert is generated, it can be an informational alert and when alerts are generated for two sequencing runs one after the other then a warning or critical alert can be generated.

If an alert is detected at the step 625 then process follows branch 1 to generate a warning alert. If the expert fault isolation rules generate an alert (625) then the system can apply further expert rules to determine a subcomponent (or part) causing the malfunction (645). A severity level for the alert can be determined by the expert fault isolation rule engine (650). The severity of alert can determine follow-up actions or workflows initiated from the alert.

If an alert is not detected at the step 625 then process follows branch 2 to generate an informational alert. A quality score for the sequencing run can be checked to see if it is above minimum required quality score (630). If the quality score is good, then no alert is generated (615). If the quality score is not good or below a required threshold, then the system can generate an information alert 660 for a suspect subcomponent. The information alert may not generate a case or a ticket for maintenance team. It may be provided as an information alert to the maintenance team and/or the operator of the sequencing instrument on a graphical user interface (GUI).

FIG. 6B presents details of processing a sequencing run by evaluating data from two reads in a sequencing run. For example, the process steps in FIG. 6B can be performed in each of the process sequence runs process steps 601 or 620. In this process flowchart, two reads in a sequencing run are processed by applying the two-stage process of classifier followed by the expert isolation rules (steps 671 and 673). If both process steps 671 and 673 isolate the same subcomponent as causing failure (step 675) then the system determines severity level of the alert at a step 679. If the two process steps 671 and 673 do not isolate the same subcomponent as causing system malfunction, then additional expert rules can be applied at a step 679 to isolate the subcomponent. The process then follows the steps described above to generate the alert.

FIG. 6C presents an example of applying expert isolation rules to classifications of multiple signal channels for two surfaces in a read to isolate a subcomponent causing system malfunction. The process starts at a step 685 when fault detection classifier 183 is invoked to classify all signal channels for two surfaces in a read of a sequencing run. There are four signal channels corresponding to the four types of nucleotides A, C, G, and T. As images can be captured from two surfaces of the flow cell in a read, therefore, up to eight signal channels can be classified by the fault detection classifier 183 for each read.

The classification results are evaluated by fault isolation rules engine 186 to isolate the subcomponent causing malfunction. FIG. 6C presents one example of a set of four rules that can be used to isolate the subcomponent.

A first example rule checks whether classifications of all signal channels from the surface are abnormal (687).

A second example rule checks whether classifications of all signal channels from bottom surface are abnormal (689). The fault detection classifier provides confidence scores of the classification of signal channels. The expert isolation rules engine can use the confidence scores from the classifier when isolating a subcomponent causing system malfunction. We describe, use of confidence score in isolating a subcomponent when presenting examples of expert rules (in expert rule 4).

A third example rule, in FIG. 6C, checks whether classifications of corresponding signal channels from the top surface and the bottom surface are highly correlated (691).

A fourth example rule checks whether the sequencing run included PhiX control library (693). PhiX control is a reliable library that can be sequenced alone and serves as a calibration control. Due to its balanced nucleotide composition, the PhiX library can be used for sequencing run quality monitoring, e.g., cluster generation, sequencing and alignment. The library provides balanced fluorescent signals at each cycle. If PhiX library is used in the sequencing run, it can help isolate sample quality issues. If cluster generation from PhiX library matches the expected results then sample may not be cause of any quality issues in base calling.

The results of the four rules are further evaluated by another expert isolation rule at a step 695 and a subcomponent is identified that may be causing system malfunction.

We now present some detailed examples of fault isolation rules including isolation of subcomponents causing failure.

Examples of Fault Isolation Rules

We present four rules as examples to illustrate isolation of subcomponents causing system malfunction.

Rule 1—M3 Alert

If M3-drift==True on both surfaces Then read alert=M3

Rule 1 tests value of "M3 drift" calculated feature. If the value is true for both surfaces of a read then expert isolation rules engine determines M3 subcomponent malfunction as the cause of system failure and generates an alert for M3 subcomponent.

Rule 2—Z-Stage Alert

If top and bottom surfaces are not correlated and
    all signal channels from top surface are classified as abnormal and
    not all signal channels from bottom surface are classified as abnormal
Then read alert=Z-stage warning Rule 2 tests three conditions before generating an alert. The first condition tests if top and bottom surfaces are not correlated. The system can check values of all channel correlation calculated features. If the values of channel correlation features are less than a predefined threshold, first condition can become true. The second condition tests if all signal channels from the top surface are classified as abnormal. The third condition test if at least one or more signal channels from the bottom surface are classified as normal. When the three condition are true, the rule generates a z-stage subcomponent alert identifying z-stage as a possible cause of system malfunction. The rule sets the severity level of the alert as "warning" which is more severe than an information alert.

Rule 3—Compensator Alert

If top and bottom surfaces are not correlated and
    not all signal channels from top surface are classified as abnormal and
    all signal channels from bottom surface are classified as abnormal
Then read alert=Compensator warning Rule 3 also tests three conditions before generating an alert. The first condition checks if top and bottom surfaces are not correlated. The second condition test if at least one or more signal channels from the top surface are classified as normal. The third condition tests if all signal channels from the bottom surface are classified as abnormal. When the three condition are true, the rule generates a compensator subcomponent alert identifying compensator as a possible cause of system malfunction. The rule sets the severity level of the alert as "warning".

Rule 4—M3 and Z-Stage Evaluation

```
1: m3_pair_bad, cam_confident=camera_pair_bad(evaluation_result)
2: if m3_pair_bad:
3:   m3_votes+=1
4:   if cam_confident:
       m3_votes+=0.5
5: led_pair_bad, led_confident=LED_pair_bad(evaluation_result)
6: if led_pair_bad:
7:   zstage_votes+=1
8:   if led_confident:
9:     zstage_votes+=0.5
10: if m3_votes—zstage_votes>=1.5:
    #if it doesn't have high phi x percentile and it is in specs
    #it is a good run and there is a high chance that optics is fine
11:  if m3_votes—zstage_votes>=1.5 and bad_nonPhix:
12:   read_df['class']=AlertDetail.M3W.name (warning,)
13:   read_df ['detail']='Problem detected in one camera. Q30 out of spec'
14:  else:
15:   read_df['class']=AlertDetail.M3.name (info alert)
16:   read_df['detail']='Problem detected in one camera.'
    #if it doesn't have high phi x percentile and it is in specs
    #it is a good run and there is a high chance that optics is fine
17: elseif zstage_votes—m3_votes>=1.5:
18:  if zstage_votes—m3_votes>=1.5 and bad_nonPhix:
19:   read_df['class']=AlertDetail.ZStage_W.name
20:   read_df['detail']='Problem detected in one LED color pair. Q30 out of spec.'
21:  else:
22:   read_df['class']=AlertDetail.ZStage.name
23:   read_df['detail']='Problem detected in one LED color pair.'
24: else:
25:  read_df['class']='NA'
26:  read_df['detail']=''
```

Rule 4 can generate alerts for M3 subcomponent and z-stage subcomponent by evaluating results received from two methods. The first method is called "camera_pair_bad" and the second method is called "LED_pair_bad". Both methods return two Booleans.

The "camera_pair_bad" method returns two Booleans. A first Boolean indicating whether the pair of M3 channels i.e., pair "AG" and pair "CT" are abnormal. Each pair of signal channels is detected by the same camera, i.e., signal channels A and G are detected by camera S2 and signal channels C and T are detected by camera S1. Degradation of focus scores in both pairs of signal channels can indicate M3 subcomponent malfunction. A second Boolean returned by the "camera_pair_bad" method indicates confidence score of the classifier. If confidence score for classification of signal channels is above a threshold, the "cam_confident" variable can be set as true and otherwise it can set as false.

The "LED_pair_bad" method also returns two Booleans. A first Boolean indicating whether the pair of LED channels i.e., pair "AC" (for red LED) and pair "GT" (for green LED) are abnormal. Each pair of signal channels is detected by illuminating the sample from excitation from a same LED. In each cycle, the z-stage is used to move the objective lens and adjust the optical focus when the LED color changes between green and red. A malfunction in the z-stage between LED activations degrades focus. Degradation of focus scores in both pairs of signal channels can indicate z-stage subcomponent malfunction. A second Boolean returned by the "LED_pair_bad" method indicates confidence score of the classifier. If confidence score for classification of signal channels is above a threshold, the "led_confident" variable can be set as true and otherwise it can set as false.

Lines 1 to 9 of the computer program code for rule 4 evaluate these Boolean values for the two methods and increments counters for M3 and z-stage votes.

At line 10 the difference between M3 votes and z-stage votes is calculated. If the difference is greater than "1.5" the logic implemented in "if" block (lines 10 to 23) is executed otherwise "else" block is executed (lines 24 and 25). It is understood that other threshold values greater than or less than 1.5 can be used when comparing the M3 and z-stage votes.

If the condition at line 10 is true, the control enters if block and checks another condition at line 11. In the if statement at line 11 two conditions are tested in a logical "AND" combination. The first condition is the difference between M3 votes and z-stage votes is compared to a value "1.5" and the second condition is "bad_nonPhix" which means that the sequencing run did not have a high percentage of PhiX control and Q30 quality score was poor. If both conditions are true in statement at line 11, lines 11 to 13 generate M3 subcomponent warning alert. The expert fault isolation rule also generates an explanation "Problem detected in one camera. Q30 out of spec" for the service technician. The explanations of alerts can help service technician in debugging the system to isolate the possible root cause of failure.

If the conditional statement at line 11 is false, else block (lines 15 and 16) is executed. These lines of code generate an information alert for the M3 subcomponent. The information alert also includes an explanation "Problem detected in one camera". The severity of information alert can be less than warning alert.

The logic implemented from lines 17 to 23 implement similar logic as described above but in this case the z-stage votes are greater than M3 votes. Therefore, the system generates alerts for z-stage subcomponent along with explanations. For example, in the if block (lines 19 and 20), the system generates z-stage alert with an explanation "Problem detected in one LED pair. Q30 out of spec." In the else block (lines 22 and 23), the system generates a z-stage alert "Problem detected in one LED color pair."

If the conditional statement at line 10 is false, the control is passed to else block (lines 25 and 26) and no alert is generated.

Figure 7B:
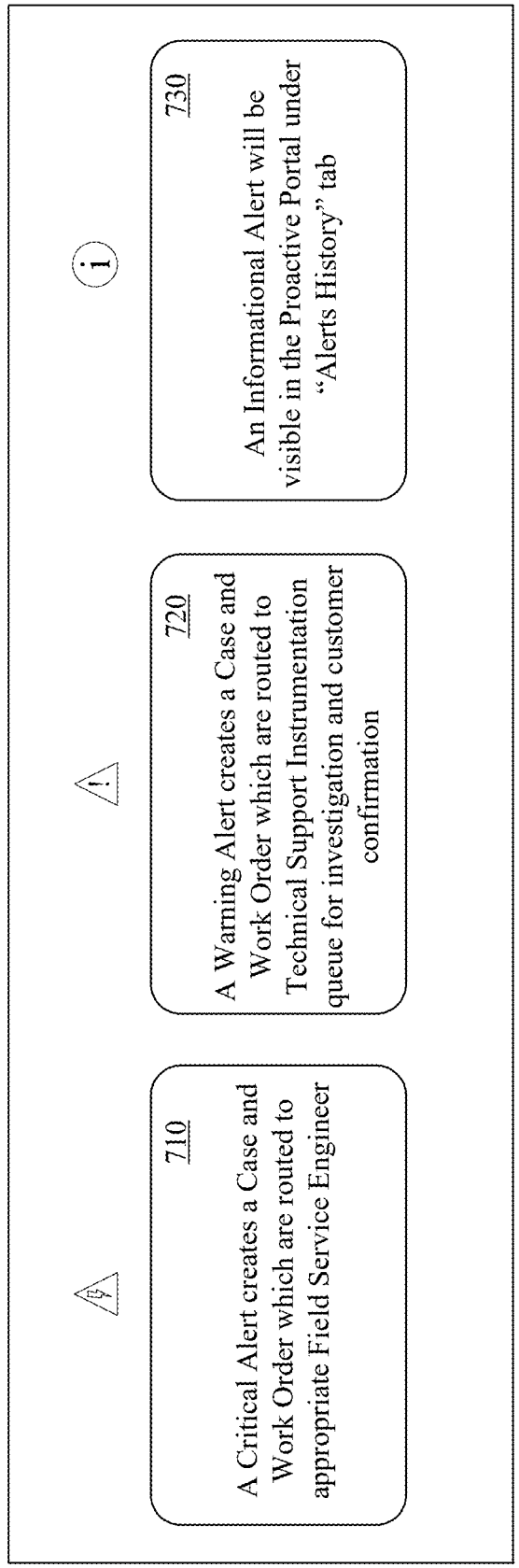
FIG. 7B presents different types of alerts corresponding to different severity levels.

FIG. 7A presents examples of alerts for M3, z-stage and compensator subcomponents. Two or three types of alerts can be generated "info" (or informational) alerts, warning alerts and, optionally, critical alerts (as in FIG. 7B.) Warning (or critical) alerts can have a higher severity level as compared to informational alerts. The system also provides an alert summary. For example, the first alert is an example of "info" alert for M3 subcomponent. The alert also includes an "info" alert summary for M3 subcomponent "Potential Optics Problem. M3 is more likely to be the cause". Alerts also includes "additional alert details". For example, for the first M3 alert, the alert detail can be "Problem detected in one Camera". Therefore, as shown in FIG. 7A, alerts generated by the expert fault isolation engine 186 can provide guidance to the service technicians and reduce incorrect subcomponent replacement. FIG. 7A presents examples of "info" and warning alerts for the three subcomponents.

FIG. 7B presents different types of alerts that can be generated by the system. In some implementations, "critical" and "warning" alerts can be combined in one category and labeled as "warning" alerts. Different types of actions can be automatically generated when an alert is generated. For example, a critical alert 710 can trigger a workflow to generate a case (or ticket) and work order for a service technician so that the technician can attend to system malfunction without delay. A warning alert 720 can also generate a case and a work order but these are directed to a queue for evaluation before a service technician is dispatched to attend to system malfunction. An informational (or info) alert 730 can be provided to an operator or user of the instrument and no case or work order is generated.

Particular Implementations

The technology disclosed is related to diagnosing system malfunction and isolating a cause of system malfunction among a plurality of replaceable subcomponents.

The technology disclosed can be practiced as a system, method, device, product, computer readable media, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

The technology disclosed can be practiced as a method of diagnosing system malfunction and isolating a cause of system malfunction among a plurality of replaceable subcomponents. The method includes applying preprocessors to time series data from at least one sequencing run. The preprocessors can detect time series abnormalities. The abnormalities can include discontinuities, drift, lack of expected correlation and trends. The preprocessors can detect time series discontinuities, detect drift, detect lack of expected correlation, and detect trends. The method includes feeding, for at least one image channel in one sequencing run, at least part of the output of the preprocessors to a trained tree-based classifier. The preprocessors can process time series for two or four image channels. The method includes receiving a classification of at least one sequencing run as abnormal indicating a system malfunction. The method includes feeding at least part of the output of the preprocessors for the abnormal sequencing run to an expert rule system. The method includes receiving a root cause isolation of the system malfunction to a particular subcomponent in need of adjustment or replacement. The subcomponent can be among a plurality of replaceable subcomponents. The method includes generating a notification of the particular subcomponent causing the system malfunction.

This method and other implementations of the technology disclosed can include one or more of the following features. In the interest of conciseness, the combinations of features disclosed in this application are not individually enumerated and are not repeated with each base set of features. Features applicable to methods, systems, and articles of manufacture are not repeated for each statutory class set of base features. The reader will understand how features identified in this section can readily be combined with base features in other statutory classes In one implementation, processing the abnormal sequencing run with the detected time series discontinuity further includes, using the sequencing run time series data generated from an optical subsystem that uses first and second LED illumination frequencies. The method includes detecting the time series discontinuities in a first time series from the first LED illumination frequency but not in a second time series from the second LED illumination frequency. The method includes generating the notification, for display on a graphical user interface, of a malfunction of a z-stage subcomponent used to correctly position an imager relative to a flow cell.

In one implementation, the method includes detecting discontinuities in a focus score by applying a smoothing filter to the focus scores time series per image channel in the sequencing run. The method includes calculating magnitudes of differences between smoothed focus scores at successive cycles in the focus scores time series per image channel in the sequencing run. The method includes detecting a number of successive cycles where the magnitudes of differences between successive cycles exceeds a predefined threshold. The method includes generating the notification, in response to detecting a malfunction of a z-stage subcomponent used to correctly position an imager relative to a flow cell. The notification can be displayed on a graphical user interface.

In one implementation, processing the abnormal sequencing run with the detected time series drift, further includes using the sequencing run time series data generated from an optical subsystem that uses a first camera and a second camera. The first camera can detect two image channels, and the second camera can detect two other image channels. The method includes detecting the drift in time series corresponding to the two image channels from the first camera but not in time series corresponding to the two other image channels from the second camera. The method includes generating the notification of a malfunction of an M3 subcomponent. The notification can be displayed on a graphical user interface.

In one implementation, the method includes detecting drift in a focus score by applying a smoothing filter to the focus scores time series per image channel in the sequencing run. The method includes calculating difference between focus scores per cycle across pairs of image channels in a plurality of image channels in the sequencing run. The method includes dividing the calculated differences in at least a first half time series and a second half time series per pair of image channels. The method includes calculating, for the pairs of image channels, an average difference value between the calculated differences for the first half time series and the second half time series per pair of image channels. The method includes comparing, for a particular pair of image channels, the average difference value with the average difference values for other pairs of image channels. The method includes generating the notification of a malfunction of an M3 subcomponent when the average difference value for the particular pair of image channels is greater than the average difference values for other pairs of image channels by a predetermined threshold.

In one implementation, the method further includes detecting lack of expected correlation by calculating a correlation between focus scores time series for a first particular image channel in a plurality of image channels in the sequencing run for a first surface and the focus scores time series for a second particular image channel in a plurality of image channels in the sequencing run for a second surface. The first particular image channel and the second particular channel detect a same nucleotide in the sequencing run. The method includes using the calculated correlation to detect the lack of expected correlation between two surfaces when the calculated correlation is below a predetermined threshold indicating a compensator or z-stage subcomponent failure. Corresponding signal channels from two surfaces are expected to have same signal pattern, when compensator or z-stage subcomponent fails, the corresponding signal channels do not have correlation which can be referred to as lack of expected correlation.

In one implementation, the method includes detecting trends in a focus score by applying a smoothing filter to the focus scores time series per image channel in the sequencing run. The method includes partitioning the focus scores time series per image channel into a predetermined number of partitions. The method includes averaging the focus scores in a first partition and a last partition. The method includes using a difference between the averaged focus score values between the first partition and the last partition and a number of focus score values per partition to calculate a slope between the last partition and the first partition of the focus scores time series per image channel. The method includes detecting the trend such as whether the slope between the last partition and the first partition of the focus scores time series is above a predetermined threshold. The calculated features including the trend feature can be used to train the fault detection classifier. The trained fault detection classifier can then classify a signal channel as abnormal using the calculated features provided as input to the classifier. The classifications of signal channels and the calculated features can be used by the expert fault isolation rules engine to indicate a subcomponent failure. Multiple expert rules may be applied in parallel or one after the other to isolate z-stage or compensator subcomponent as causing malfunction.

In one implementation, the method further includes isolating the root cause of malfunction in two or more sequencing runs before generating the notification of subcomponent malfunction.

The sequencing run comprises a plurality of cycles. A cycle in the plurality of cycles can comprise chemical processing, image capture and image processing actions.

The time series data can include a focus score per image channel. Determining the focus score includes calculating a time series of focus scores based on per cycle average FWHM for a flow cell from a per image tile FWHM averages.

The time series data can include an intensity value per image channel. Determining the intensity value can include calculating a time series of intensity values based on per cycle average intensity for a flow cell from a per image tile intensity value averages.

The notification of the particular subcomponent causing the system malfunction can include an explanation including an identified possible defect in the particular subcomponent causing the system malfunction.

In one implementation, receiving the classification of the at least one sequencing run as abnormal further includes indicating a system malfunction.

The root cause isolation of the system malfunction to the particular subcomponent can indicate the particular subcomponent in need of adjustment or replacement, among the plurality of replaceable subcomponents.

The malfunction of the z-stage subcomponent which is used to correctly position an imager relative to a flow cell can result in poor focus quality of captured images.

Some expert rules may run successfully without using abnormal classification from fault detection classifier. For example, the expert rules for isolation M3 subcomponent can use output from the drift detector. If the output from drift detector detects drift in at least one signal channel, the expert fault isolation rules engine can generate an alert for M3 subcomponent. In one implementation, if the output from drift detector detects drift in all four signal channels, the expert fault isolation rules engine can generate an alert for M3 subcomponent. Similarly, the expert fault isolation rules engine can use output from mid-process vibration detector to isolate z-stage subcomponent malfunction. The second method implementation of the technology includes applying preprocessors to time series data from at least one sequencing run. The preprocessors can detect time series abnormalities. The abnormalities can include discontinuities, drift, lack of expected correlation and trends. The preprocessors can detect time series discontinuities, detect drift, detect lack of expected correlation, and detect trends. The method includes feeding at least part of the output of the preprocessors to an expert rule system. The method includes receiving a root cause isolation of the system malfunction to a particular subcomponent in need of adjustment or replacement. The subcomponent can be among a plurality of replaceable subcomponents. The method includes generating a notification of the particular subcomponent causing the system malfunction.

Other implementations consistent with methods may include a non-transitory computer readable storage medium storing instructions executable by a processor to perform any of the methods described above. Yet another implementation may include a system with memory loaded from a computer readable storage medium with program instructions to perform the any of the methods described above. The system can be loaded from either a transitory or a non-transitory computer readable storage medium.

Aspects of the technology disclosed can be practiced as a system that includes one or more processors coupled to memory. The memory is loaded with computer instructions to diagnose system malfunction and isolate a cause of system malfunction among a plurality of replaceable subcomponents. The system includes logic to apply preprocessors to time series data from at least one sequencing run. The preprocessors can detect time series discontinuities, detect drift, detect lack of expected correlation, and that detect trends. The system includes logic to feed, for at least one image channel in one sequencing run, at least part of the output of the preprocessors to a trained tree-based classifier. The preprocessors can process time series for two or four image channels. The system includes logic to receive a classification of the at least one sequencing run as abnormal indicating a system malfunction. The system includes feeding at least part of the output of the preprocessors for the abnormal sequencing run to an expert rule system. The system includes receiving a root cause isolation of the system malfunction to a particular subcomponent in need of adjustment or replacement, among the plurality of replaceable subcomponents. The system includes logic to generate a notification of the particular subcomponent causing the system malfunction.

A second system implementation of the technology includes one or more processors coupled to memory. The memory is loaded with computer instructions to diagnose system malfunction and isolate a cause of system malfunction among a plurality of replaceable subcomponents. The system includes logic to apply preprocessors to time series data from at least one sequencing run. The preprocessors can detect time series discontinuities, detect drift, detect lack of expected correlation, and that detect trends. The preprocessors can process time series for two or four image channels. The system includes feeding at least part of the output of the preprocessors to an expert rule system. The system includes receiving a root cause isolation of the system malfunction to a particular subcomponent in need of adjustment or replacement, among the plurality of replaceable subcomponents. The system includes logic to generate a notification of the particular subcomponent causing the system malfunction.

The computer implemented systems can incorporate any of the features of method described immediately above or throughout this application that apply to the method implemented by the system. In the interest of conciseness, alternative combinations of system features are not individually enumerated. Features applicable to systems, methods, and articles of manufacture are not repeated for each statutory class set of base features. The reader will understand how features identified in this section for one statutory class can readily be combined with base features in other statutory classes.

Other implementations may include a non-transitory computer readable storage medium storing instructions executable by a processor to perform functions of the system described above. Yet another implementation may include a method performing the functions of the system described above.

As an article of manufacture, rather than a method, a non-transitory computer readable medium (CRM) can be loaded with program instructions executable by a processor. The program instructions when executed, implement the computer-implemented method described above. Alternatively, the program instructions can be loaded on a non-transitory CRM and, when combined with appropriate hardware, become a component of one or more of the computer-implemented systems that practice the method disclosed.

Each of the features discussed in this particular implementation section for the method implementation apply equally to CRM implementation. As indicated above, all the method features are not repeated here, in the interest of conciseness, and should be considered repeated by reference.

Computer System

Figure 8:
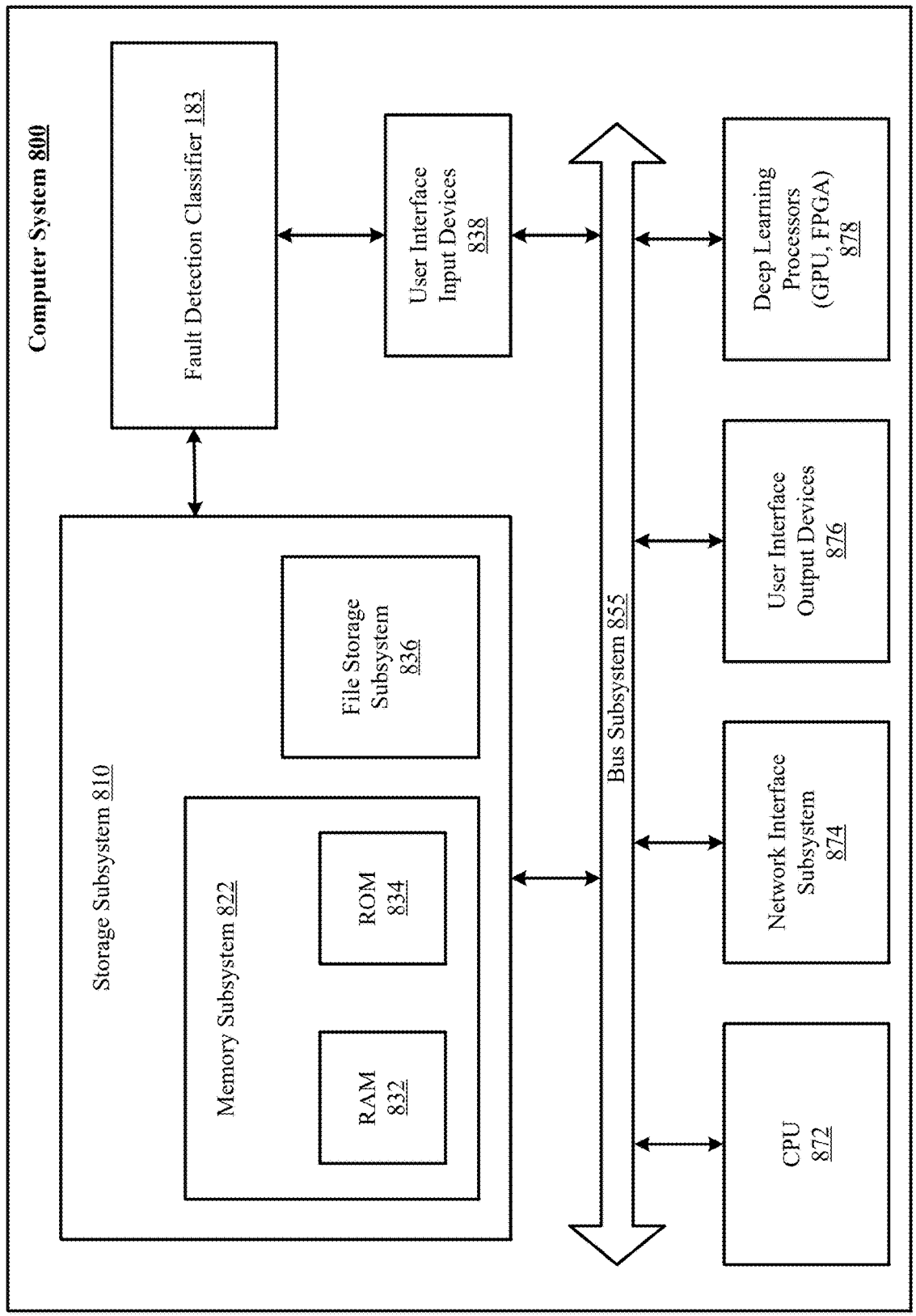
FIG. 8 is a simplified block diagram of a computer system that can be used to implement the technology disclosed.

FIG. 8 is a simplified block diagram of a computer system 800 that can be used to implement the technology disclosed. Computer system typically includes at least one processor 872 that communicates with a number of peripheral devices via bus subsystem 855. These peripheral devices can include a storage subsystem 810 including, for example, memory subsystem 822 and a file storage subsystem 836, user interface input devices 838, user interface output devices 876, and a network interface subsystem 874. The input and output devices allow user interaction with computer system. Network interface subsystem provides an interface to outside networks, including an interface to corresponding interface devices in other computer systems.

In one implementation, the fault detection classifier 183 is communicably linked to the storage subsystem and user interface input devices.

User interface input devices 838 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

User interface output devices 876 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system to the user or to another machine or computer system.

Storage subsystem 810 stores programming and data constructs that provide the functionality of some or all of the modules and methods described herein. These software modules are generally executed by processor alone or in combination with other processors.

Memory used in the storage subsystem can include a number of memories including a main random access memory (RAM) 832 for storage of instructions and data during program execution and a read only memory (ROM) 834 in which fixed instructions are stored. The file storage subsystem 836 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem in the storage subsystem, or in other machines accessible by the processor.

Bus subsystem 855 provides a mechanism for letting the various components and subsystems of computer system communicate with each other as intended. Although bus subsystem is shown schematically as a single bus, alternative implementations of the bus subsystem can use multiple busses.

Computer system itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system depicted in FIG. 8 is intended only as a specific example for purposes of illustrating the technology disclosed. Many other configurations of computer system are possible having more or less components than the computer system depicted in FIG. 8.

The computer system 800 includes GPUs or FPGAs 878. It can also include machine learning processors hosted by machine learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

What is claimed is:

1. A computer-implemented method of diagnosing system malfunction and isolating a cause of the system malfunction among a plurality of replaceable subcomponents, the method including:
   applying, to time series data from at least one sequencing run, preprocessors that detect time series abnormalities, wherein time series abnormalities include discontinuities, drift, lack of expected correlation, and trends, wherein the discontinuities are detected in focus scores by:
      applying a smoothing filter to the focus scores time series per image channel in the sequencing run;
      calculating magnitudes of differences between the smoothed focus scores at successive cycles in the focus scores time series per image channel in the sequencing run;
      detecting a number of successive cycles where the magnitudes of differences between successive cycles exceeds a predefined threshold;
   for at least one image channel in one sequencing run, feeding at least part of the output of the preprocessors to a trained tree-based classifier and receiving a classification of the at least one sequencing run as abnormal;
   feeding at least part of the output of the preprocessors for the abnormal sequencing run to an expert rule system and receiving a root cause isolation of the system malfunction to a particular subcomponent; and
   generating at least one notification of the particular subcomponent causing the system malfunction for display on a graphical user interface, wherein the at least one notification comprises, based on the detecting the number of successive cycles where the magnitudes of differences between the successive cycles exceeds the predefined threshold, an indication of a malfunction of a z-stage subcomponent used to correctly position an imager relative to a flow cell.

2. The method of claim 1, wherein processing the abnormal sequencing run with the detected time series discontinuity further includes:
   using the sequencing run time series data generated from an optical subsystem that uses first and second LED illumination frequencies;
   detecting the time series discontinuities in a first time series from the first LED illumination frequency but not in a second time series from the second LED illumination frequency; and
   wherein the at least one notification comprising the indication of the malfunction of the z-stage subcomponent used to correctly position the imager relative to the flow cell is based on the detected discontinuities in the first time series from the first LED illumination frequency but not in the second time series from the second LED illumination frequency.

3. The method of claim 2, wherein the malfunction of the z-stage subcomponent, used to correctly position an imager relative to a flow cell, results in poor focus quality of captured images.

4. The method of claim 1, wherein processing the abnormal sequencing run with the detected time series drift, further includes:
   using the sequencing run time series data generated from an optical subsystem that uses a first camera and a second camera, wherein the first camera detects two image channels, and the second camera detects two other image channels;

detecting the drift in time series corresponding to the two image channels from the first camera but not in time series corresponding to the two other image channels from the second camera; and wherein the at least one notification comprises an indication of a malfunction of an M3 subcomponent based on the detected drift.

5. The method of claim 1, further including isolating the root cause of malfunction in two or more sequencing runs before generating the at least one notification of subcomponent malfunction.

6. The method of claim 1, wherein the root cause isolation of the system malfunction to the particular subcomponent indicates the particular subcomponent in need of adjustment or replacement, among the plurality of replaceable subcomponents.

7. A computer-implemented method of diagnosing system malfunction and isolating a cause of system malfunction among a plurality of replaceable subcomponents, the method including:

applying, to time series data from at least one sequencing run, preprocessors that detect time series abnormalities, wherein time series abnormalities include discontinuities, drift, lack of expected correlation, and trends, wherein the drift is detected in focus scores by:

applying a smoothing filter to the focus scores time series per image channel in the sequencing run;

calculating difference between the focus scores per cycle across pairs of image channels in a plurality of image channels in the sequencing run;

dividing the calculated differences in at least a first half time series and a second half time series per pair of image channels;

calculating, for the pairs of image channels, an average difference value between the calculated differences for the first half time series and the second half time series per pair of image channels and comparing, for a particular pair of image channels, the average difference value with the average difference values for other pairs of image channels; and for at least one image channel in one sequencing run, feeding at least part of the output of the preprocessors to a trained tree-based classifier and receiving a classification of the at least one sequencing run as abnormal;

feeding at least part of the output of the preprocessors for the abnormal sequencing run to an expert rule system and receiving a root cause isolation of the system malfunction to a particular subcomponent; and generating at least one notification for display on a graphical user interface of the particular subcomponent causing the system malfunction, wherein the at least one notification comprises an indication of a malfunction of an M3 subcomponent based on the average difference value for the particular pair of image channels being greater than the average difference values for other pairs of image channels by a predetermined threshold.

8. The method of claim 7, wherein processing the abnormal sequencing run with the detected time series discontinuity further includes:

using the sequencing run time series data generated from an optical subsystem that uses first and second LED illumination frequencies;

detecting the time series discontinuities in a first time series from the first LED illumination frequency but not in a second time series from the second LED illumination frequency; and wherein the at least one notification comprises, based on the detected time series discontinuities in the first time series from the first LED illumination frequency but not in the second time series from the second LED illumination frequency, an indication of a malfunction of a z-stage subcomponent used to correctly position an imager relative to a flow cell.

9. The method of claim 8, wherein the malfunction of the z-stage subcomponent, used to correctly position an imager relative to a flow cell, results in poor focus quality of captured images.

10. The method of claim 7, wherein processing the abnormal sequencing run with the detected time series drift, further includes:

using the sequencing run time series data generated from an optical subsystem that uses a first camera and a second camera wherein the first camera detects two image channels, and the second camera detects two other image channels;

detecting the drift in time series corresponding to the two image channels from the first camera but not in time series corresponding to the two other image channels from the second camera; and wherein the at least one notification of the malfunction of the M3 subcomponent is based on the detected drift in the time series corresponding to the two image channels from the first camera but not in the time series corresponding to the two other image channels from the second camera.

11. The method of claim 7, further including isolating the root cause of malfunction in two or more sequencing runs before generating the at least one notification of subcomponent malfunction.

12. The method of claim 7, wherein the root cause isolation of the system malfunction to the particular subcomponent indicates the particular subcomponent in need of adjustment or replacement, among the plurality of replaceable subcomponents.

13. A computer-implemented method of diagnosing system malfunction and isolating a cause of system malfunction among a plurality of replaceable subcomponents, the method including:

applying, to time series data from at least one sequencing run, preprocessors that detect time series abnormalities, wherein time series abnormalities include discontinuities, drift, lack of expected correlation, and trends, wherein the lack of expected correlation is detected by:

calculating a correlation between the focus scores time series for a first particular image channel in a plurality of image channels in the sequencing run for a first surface and the focus scores time series for a second particular image channel in a plurality of image channels in the sequencing run for a second surface wherein the first particular image channel and the second particular channel detect a same nucleotide in the sequencing run; and using the calculated correlation to detect the lack of expected correlation between two surfaces when the calculated correlation is below a predetermined threshold indicating a compensator subcomponent failure;

for at least one image channel in one sequencing run, feeding at least part of the output of the preprocessors to a trained tree-based classifier and receiving a classification of the at least one sequencing run as abnormal;

feeding at least part of the output of the preprocessors for the abnormal sequencing run to an expert rule system and receiving a root cause isolation of the system malfunction to a particular subcomponent; and generating at least one notification of the particular subcomponent causing the system malfunction.

14. The method of claim 13, wherein processing the abnormal sequencing run with the detected time series discontinuity further includes:

using the sequencing run time series data generated from an optical subsystem that uses first and second LED illumination frequencies;

detecting the time series discontinuities in a first time series from the first LED illumination frequency but not in a second time series from the second LED illumination frequency; and wherein the at least one notification comprises, based on the detected time series discontinuities in the first time series from the first LED illumination frequency but not in the second time series from the second LED illumination frequency, an indication of a malfunction of a z-stage subcomponent used to correctly position an imager relative to a flow cell.

15. The method of claim 14, wherein the malfunction of the z-stage subcomponent, used to correctly position an imager relative to a flow cell, results in poor focus quality of captured images.

16. The method of claim 13, wherein processing the abnormal sequencing run with the detected time series drift, further includes:

using the sequencing run time series data generated from an optical subsystem that uses a first camera and a second camera wherein the first camera detects two image channels, and the second camera detects two other image channels;

detecting the drift in time series corresponding to the two image channels from the first camera but not in time series corresponding to the two other image channels from the second camera; and wherein the at least one notification comprises an indication of a malfunction of an M3 subcomponent based on the detected drift in time series corresponding to the two image channels from the first camera but not in time series corresponding to the two other image channels from the second camera.

17. The method of claim 13, further including isolating the root cause of malfunction in two or more sequencing runs before generating the at least one notification of subcomponent malfunction.

18. The method of claim 13, wherein the root cause isolation of the system malfunction to the particular subcomponent indicates the particular subcomponent in need of adjustment or replacement, among the plurality of replaceable subcomponents.

19. A computer-implemented method of diagnosing system malfunction and isolating a cause of system malfunction among a plurality of replaceable subcomponents, the method including:

applying, to time series data from at least one sequencing run, preprocessors that detect time series abnormalities, wherein time series abnormalities include discontinuities, drift, lack of expected correlation, and trends, wherein the trends are detected in focus scores by:

applying a smoothing filter to the focus scores time series per image channel in the sequencing run;

partitioning the focus scores time series per image channel into a predetermined number of partitions;

averaging the focus scores in a first partition and a last partition;

using a difference between the averaged focus score values between the first partition and the last partition and a number of focus score values per partition to calculate a slope between the last partition and the first partition of the focus scores time series per image channel; and detecting the trend indicating a z-stage failure or a compensator failure if the slope between the last partition and the first partition of the focus scores time series is above a predetermined threshold;

for at least one image channel in one sequencing run, feeding at least part of the output of the preprocessors to a trained tree-based classifier and receiving a classification of the at least one sequencing run as abnormal;

feeding at least part of the output of the preprocessors for the abnormal sequencing run to an expert rule system and receiving a root cause isolation of the system malfunction to a particular subcomponent; and generating at least one notification of the particular subcomponent causing the system malfunction.

20. The method of claim 19, wherein processing the abnormal sequencing run with the detected time series discontinuity further includes:

using the sequencing run time series data generated from an optical subsystem that uses first and second LED illumination frequencies;

detecting the time series discontinuities in a first time series from the first LED illumination frequency but not in a second time series from the second LED illumination frequency; and wherein the at least one notification comprises, based on the detected time series discontinuities in the first time series from the first LED illumination frequency but not in the second time series from the second LED illumination frequency, an indication of a malfunction of a z-stage subcomponent used to correctly position an imager relative to a flow cell.

21. The method of claim 20, wherein the malfunction of the z-stage subcomponent, used to correctly position an imager relative to a flow cell, results in poor focus quality of captured images.

22. The method of claim 19, wherein processing the abnormal sequencing run with the detected time series drift, further includes:

using the sequencing run time series data generated from an optical subsystem that uses a first camera and a second camera wherein the first camera detects two image channels, and the second camera detects two other image channels;

detecting the drift in time series corresponding to the two image channels from the first camera but not in time series corresponding to the two other image channels from the second camera; and wherein the at least one notification comprises an indication of a malfunction of an M3 subcomponent based on the detected drift in time series corresponding to the two image channels from the first camera but not in time series corresponding to the two other image channels from the second camera.

23. The method of claim 19, further including isolating the root cause of malfunction in two or more sequencing runs before generating the at least one notification of subcomponent malfunction.

24. The method of claim 19, wherein the root cause isolation of the system malfunction to the particular subcomponent indicates the particular subcomponent in need of adjustment or replacement, among the plurality of replaceable subcomponents.

25. A system including one or more processors coupled to memory, the memory loaded with computer instructions to diagnose system malfunction and isolate a cause of system malfunction among a plurality of replaceable subcomponents, the instructions, when executed on the one or more processor, are configured to cause the one or more processors to:

apply, to time series data from at least one sequencing run, preprocessors that detect time series abnormalities, wherein time series abnormalities include discontinuities, drift, lack of expected correlation, and trends, wherein the instructions are configured to cause the one or more processors to detect the discontinuities in focus scores by being configured to cause the one or more processors to:

apply a smoothing filter to the focus scores time series per image channel in the sequencing run;

calculate magnitudes of differences between the smoothed focus scores at successive cycles in the focus scores time series per image channel in the sequencing run;

detect a number of successive cycles where the magnitudes of differences between successive cycles exceeds a predefined threshold;

for at least one image channel in one sequencing run, feed at least part of the output of the preprocessors to a trained tree-based classifier and receiving a classification of the at least one sequencing run as abnormal;

feed at least part of the output of the preprocessors for the abnormal sequencing run to an expert rule system and receiving a root cause isolation of the system malfunction to a particular subcomponent; and generate at least one notification of the particular subcomponent causing the system malfunction for display on a graphical user interface, wherein the at least one notification, based on the detection of the number of successive cycles where the magnitudes of differences between the successive cycles exceeds the predefined threshold, an indication of a malfunction of a z-stage subcomponent used to correctly position an imager relative to a flow cell.

26. The system of claim 25, wherein the instructions being configured to cause the one or more processors to process the abnormal sequencing run with the detected time series discontinuity, further comprises the instructions being configured to cause the one or more processors to:

use the sequencing run time series data generated from an optical subsystem that uses first and second LED illumination frequencies;

detect the time series discontinuities in a first time series from the first LED illumination frequency but not in a second time series from the second LED illumination frequency; and wherein the at least one notification comprises an indication of a malfunction of a z-stage subcomponent used to correctly position an imager relative to a flow cell.

27. The system of claim 25, wherein the instructions being configured to cause the one or more processors to process the abnormal sequencing run with the detected time series drift, further comprises the instructions being configured to cause the one or more processors to:

use the sequencing run time series data generated from an optical subsystem that uses a first camera and a second camera wherein the first camera detects two image channels, and the second camera detects two other image channels;

detect the drift in time series corresponding to the two image channels from the first camera but not in time series corresponding to the two other image channels from the second camera; and wherein the at least one notification comprises an indication of a malfunction of an M3 subcomponent based on the detected drift.

28. A system including one or more processors coupled to memory, the memory loaded with computer instructions to diagnose system malfunction and isolate a cause of system malfunction among a plurality of replaceable subcomponents, the instructions, when executed on the one or more processors, are configured to cause the one or more processors to:

apply, to time series data from at least one sequencing run, preprocessors that detect time series abnormalities, wherein time series abnormalities include discontinuities, drift, lack of expected correlation, and trends, wherein the instructions are further configured to cause the one or more processors to detect the drift in focus scores by being configured to cause the one or more processors to:

apply a smoothing filter to the focus scores time series per image channel in the sequencing run;

calculate difference between the focus scores per cycle across pairs of image channels in a plurality of image channels in the sequencing run;

divide the calculated differences in at least a first half time series and a second half time series per pair of image channels;

calculate, for the pairs of image channels, an average difference value between the calculated differences for the first half time series and the second half time series per pair of image channels and comparing, for a particular pair of image channels, the average difference value with the average difference values for other pairs of image channels; and for at least one image channel in one sequencing run, feed at least part of the output of the preprocessors to a trained tree-based classifier and receiving a classification of the at least one sequencing run as abnormal;

feed at least part of the output of the preprocessors for the abnormal sequencing run to an expert rule system and receiving a root cause isolation of the system malfunction to a particular subcomponent; and generate at least one notification of the particular subcomponent causing the system malfunction, wherein the at least one notification comprises an indication of a malfunction of an M3 subcomponent to focus a plurality of tiles when the average difference value for the particular pair of image channels is greater than the average difference values for other pairs of image channels by a predetermined threshold.

29. The system of claim 28, wherein the instructions being configured to cause the one or more processors to process the abnormal sequencing run with the detected time series discontinuity, further comprises the instructions being configured to cause the one or more processors to:

use the sequencing run time series data generated from an optical subsystem that uses first and second LED illumination frequencies;

detect the time series discontinuities in a first time series from the first LED illumination frequency but not in a second time series from the second LED illumination frequency; and wherein the at least one notification comprises an indication of a malfunction of a z-stage subcomponent used to correctly position an imager relative to a flow cell.

30. The system of claim 28, wherein the instructions being configured to cause the one or more processors to process the abnormal sequencing run with the detected time series drift, further comprises the instructions being configured to cause the one or more processors to:

use the sequencing run time series data generated from an optical subsystem that uses a first camera and a second camera wherein the first camera detects two image channels, and the second camera detects two other image channels;

detect the drift in time series corresponding to the two image channels from the first camera but not in time series corresponding to the two other image channels from the second camera; and wherein the at least one notification comprises the indication of the malfunction of the M3 subcomponent based on the detected drift.

31. A non-transitory computer readable storage medium impressed with computer program instructions to diagnose system malfunction and isolate a cause of system malfunction among a plurality of replaceable subcomponents, the instructions, when executed on a processor, are configured to cause the processor to:

apply, to time series data from at least one sequencing run, preprocessors that detect time series abnormalities, wherein time series abnormalities include discontinuities, drift, lack of expected correlation, and trends, wherein the instructions are configured to cause the processor to detect the lack of expected correlation by being configured to cause the processor to:

calculate a correlation between focus scores time series for a first particular image channel in a plurality of image channels in the sequencing run for a first surface and the focus scores time series for a second particular image channel in a plurality of image channels in the sequencing run for a second surface wherein the first particular image channel and the second particular channel detect a same nucleotide in the sequencing run; and use the calculated correlation to detect the lack of expected correlation between two surfaces when the calculated correlation is below a predetermined threshold indicating a compensator subcomponent failure;

for at least one image channel in one sequencing run, feed at least part of the output of the preprocessors to a trained tree-based classifier and receiving a classification of the at least one sequencing run as abnormal;

feed at least part of the output of the preprocessors for the abnormal sequencing run to an expert rule system and receiving a root cause isolation of the system malfunction to a particular subcomponent; and generate at least one notification of the particular subcomponent causing the system malfunction.

32. The non-transitory computer readable storage medium of claim 31, wherein the sequencing run comprises a plurality of cycles, a cycle in the plurality of cycles comprising chemical processing, image capture and image processing actions.

33. The non-transitory computer readable storage medium of claim 31, wherein the time series data includes a focus score per image channel, wherein the instructions being configured to cause the processor to determine the focus score comprises the instructions being configured to cause the processor to:

calculate a time series of focus scores based on per cycle average FWHM for a flow cell from a per image tile FWHM averages.

34. A non-transitory computer readable storage medium impressed with computer program instructions to diagnose system malfunction and isolate a cause of system malfunction among a plurality of replaceable subcomponents, the instructions, when executed on a processor, are configured to cause the processor to:

apply to time series data from at least one sequencing run, preprocessors that detect time series abnormalities, wherein time series abnormalities include discontinuities, drift, lack of expected correlation, and trends, wherein the instructions are configured to cause the processor to detect the trends in focus scores by being configured to cause the processor to:

apply a smoothing filter to the focus scores time series per image channel in the sequencing run;

partition the focus scores time series per image channel into a predetermined number of partitions;

average the focus scores in a first partition and a last partition;

use a difference between the averaged focus score values between the first partition and the last partition and a number of focus score values per partition to calculate a slope between the last partition and the first partition of the focus scores time series per image channel; and detect the trend indicating a z-stage failure or a compensator failure if the slope between the last partition and the first partition of the focus scores time series is above a predetermined threshold;

for at least one image channel in one sequencing run, feed at least part of the output of the preprocessors to a trained tree-based classifier and receiving a classification of the at least one sequencing run as abnormal;

feed at least part of the output of the preprocessors for the abnormal sequencing run to an expert rule system and receiving a root cause isolation of the system malfunction to a particular subcomponent; and generate at least one notification of the particular subcomponent causing the system malfunction.

35. The non-transitory computer readable storage medium of claim 34, wherein the sequencing run comprises a plurality of cycles, a cycle in the plurality of cycles comprising chemical processing, image capture and image processing actions.

36. The non-transitory computer readable storage medium of claim 34, wherein the time series data includes a focus score per image channel, wherein the instructions being configured to cause the processor to determine the focus score comprises the instructions being configured to cause the processor to:

calculate a time series of focus scores based on per cycle average FWHM for a flow cell from a per image tile FWHM averages.

* * * * *

UNITED STATES PATENT AND TRADEMARK OFFICE
CERTIFICATE OF CORRECTION

| | |
|---|---|
| PATENT NO. | : 12,393,187 B2 |
| APPLICATION NO. | : 17/710665 |
| DATED | : August 19, 2025 |
| INVENTOR(S) | : Yasmin Sahaf |

Page 1 of 1

It is certified that error appears in the above-identified patent and that said Letters Patent is hereby corrected as shown below:

In the Claims

In Column 39, Line 15, Claim 25, delete "processor," and insert -- processors, --, therefor.

In Column 42, Line 19, Claim 34, delete "apply" and insert -- apply, --, therefor.

Signed and Sealed this
Seventh Day of October, 2025

John A. Squires
*Director of the United States Patent and Trademark Office*